(12) United States Patent
Krajewski et al.

(10) Patent No.: US 9,828,323 B2
(45) Date of Patent: Nov. 28, 2017

(54) PROCESS FOR PREPARATION OF MK-7 TYPE OF VITAMIN K2

(71) Applicant: NATTOPHARMA R&D LTD, Nicosia (CY)

(72) Inventors: Krzysztof Krajewski, Warsaw (PL); Andrzej Kutner, Warsaw (PL); Jadwiga Dzikowska, Blonie (PL); Regina Gutowska, Sieraków (PL); Marek Napiórkowski, Warsaw (PL); Jerzy Winiarski, Warsaw (PL); Marek Kubiszewski, Iłow (PL); Łukasz Jedynak, Sosnowiec (PL); Jacek Morzycki, Białystok (PL); Stanislaw Witkowski, Białystok (PL); Aneta Baj, Białystok (PL); Piotr Wałejko, Białystok (PL)

(73) Assignee: Nattopharma R & D Ltd., Nicosia (CY)

( * ) Notice: Subject to any disclaimer, the term of this patent is extended or adjusted under 35 U.S.C. 154(b) by 0 days.

(21) Appl. No.: 14/435,260

(22) PCT Filed: Oct. 11, 2013

(86) PCT No.: PCT/PL2013/000132
§ 371 (c)(1),
(2) Date: Apr. 13, 2015

(87) PCT Pub. No.: WO2014/058330
PCT Pub. Date: Apr. 17, 2014

(65) Prior Publication Data
US 2015/0291498 A1 Oct. 15, 2015

Related U.S. Application Data

(60) Provisional application No. 61/771,741, filed on Mar. 1, 2013.

(30) Foreign Application Priority Data

Oct. 12, 2012 (PL) .......................................... 401195

(51) Int. Cl.
*C07C 49/553* (2006.01)
*C07C 315/04* (2006.01)
(Continued)

(52) U.S. Cl.
CPC ............ *C07C 49/553* (2013.01); *C07C 41/18* (2013.01); *C07C 45/27* (2013.01); *C07C 315/04* (2013.01)

(58) Field of Classification Search
CPC ....... C07C 315/04; C07C 41/18; C07C 46/02; C07C 49/553; C07C 67/00; C07C 317/22; C07C 29/147; C07C 317/18; C07C 43/215
See application file for complete search history.

(56) References Cited

U.S. PATENT DOCUMENTS 4,199,531 A 4/1980 Terao et al.
2011/0118374 A1 5/2011 Schneider et al.

FOREIGN PATENT DOCUMENTS

KR 1020050089969 * 3/2007 ........... C07C 315/04
WO 2010003500 A1 1/2010
(Continued)

OTHER PUBLICATIONS

Min et al., "The Friedel-Crafts Allylation of a Prenyl Group Stabilized by a Sulfone Moiety: Expeditious Syntheses of Ubiquinones and menaquinones", The Journal of Organic Chemistry, American Cancer Society, vol. 68, No. 20, 2003, pp. 7925-7927. (Abstract Only).

*Primary Examiner* — Rosalynd A Keys
(74) *Attorney, Agent, or Firm* — Rothwell, Figg, Ernst & Manbeck, P.C.

(57) ABSTRACT

Process for preparation of MK-7 type of vitamin K2 is characterized by attaching hexaprenyl chain of "all-trans" configuration to monoprenyl derivative of menadiol following "1+6" synthetic strategy. According to the invention, a-sulfonyl carbanion generated in situ from the protected monoprenyl menadiol of the formula (II), wherein $R_1$ represents $C_{1-3}$-alkyl group, is reacted with hexaprenyl halide of the formula (VII), wherein X represents halogen atom, preferably bromine, both Z' and Z' represent H or one of Z' and Z" represents H and the other represents phenylsulfonyl group —$SO_2Ph$ in the alkylation reaction. The hexaprenyl halide of formula (VII) is obtained by coupling two triprenyl units in alkylation reaction, with or without separation of the intermediates.

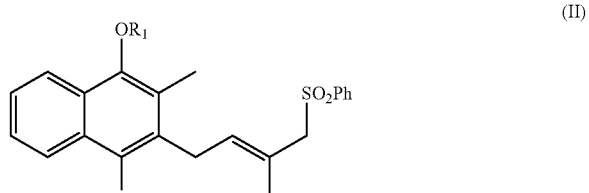

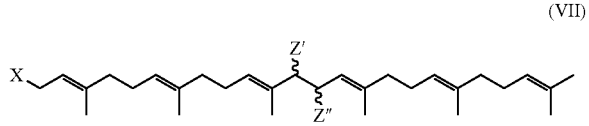

24 Claims, 2 Drawing Sheets

(51) Int. Cl.
*C07C 41/18* (2006.01)
*C07C 45/27* (2006.01)

(56) References Cited

FOREIGN PATENT DOCUMENTS

WO    WO2010034999 A1 *   4/2010  ............. C07C 46/02
WO    2011117324 A2    9/2011

* cited by examiner

PROCESS FOR PREPARATION OF MK-7 TYPE OF VITAMIN K2

CROSS REFERENCE TO RELATED APPLICATION

This application is a 35 U.S.C. 371 National Phase Entry Application from PCT/PL2013/000132, filed Oct. 11, 2013, which claims the benefit of PL Patent Application No. P.401195 filed on Oct. 12, 2012 and U.S. Provisional 61/771,741 filed on Mar. 1, 2013, the disclosures of which are incorporated herein in their entirety by reference.

FIELD OF INVENTION

The present invention relates to the process for preparation of MK-7 type of vitamin $K_2$.

Vitamins $K_2$ play an important role in the blood coagulation cascade and the bones supplementation. The synthetic MK-7 type of vitamin $K_2$ could be used in dietary supplements.

BACKGROUND OF THE INVENTION

Vitamins K are structurally related compounds, that share the 2-methyl-1,4-naphthoquinone ring but differ in the saturation and the number of attached side chains. The group of vitamins K includes two natural vitamers: vitamin $K_1$ (also known as phylloquinone or phytomenadione), containing phytin residue at C-3 position, vitamins $K_2$ (called menaquinones or pharnoquinones), characterized by the menadione structure with polyprenyl side chain at C-3 position, as well as a number of easily fat and water soluble synthetic derivatives such as vitamin $K_3$ (menadione). Molecular structures of different vitamins K are represented by the formulae depicted below:

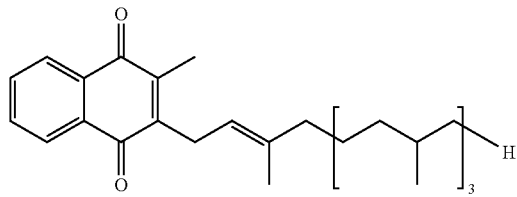

$K_1$ (phylloquinone)

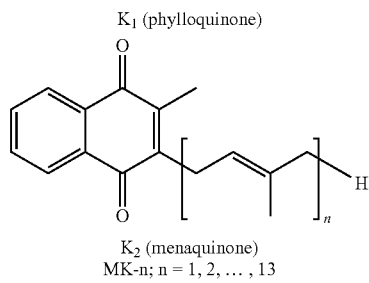

$K_2$ (menaquinone)
MK-n; n = 1, 2, ... , 13

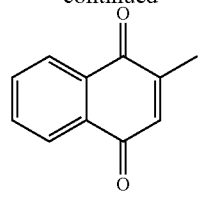

$K_3$ (menadione)

Menachinones (MK-n) have the different isoprene units number in the side chain (n=1-13). Different biological activity and bioavailability of menaquinones (MK-n) result from the chain length and the number of unsaturated bonds present in that side chain [*Chemistry of Natural Compound* 2007, 43(3), 277-281].

Vitamin K, as a cofactor of γ-carboxylase, is involved in posttranslational γ-carboxylation of certain glutamate residues in precursor proteins PIVKA. Vitamin K is necessary for the biosynthesis and maintenance at the appropriate level of coagulation factors II, VII, IX and X, osteocalcin, osteopontin, osteonectin and also calcium binding protein in kidneys, placenta and lungs. Vitamin K is involved in the coagulation cascade in animals and its presence is essential for the proper synthesis of blood clotting proteins, participating in the coagulation homeostasis. It also contributes to strong bones formation, preventing from osteoporosis development. Vitamin K also exerts anti-bacterial, anti-fungal, anti-inflammatory and pain relief activities. Recently, it has been proved that vitamin $K_2$ may substantially affect the condition of arterial walls and blood circulation.

Vitamin K is not produced by human tissue. It is found in green plants, such as green leafy vegetables (spinach, broccoli, cabbage, lettuce, green tea). Vitamin $K_2$ is synthesized by bacteria, therefore it is present in abundance in fermented food products, like for example: cheese, yogurt, sauerkraut. Meat also contains vitamin K, and MK-7 is found in large quantities (about 10 μg/g) in fermented soybean seeds. Since vitamin K is produced by intestinal bacteria, the human body is usually provided with enough quantities of this vitamin. However, it is observed that a long term treatment with sulfonamides and antibiotics may cause deficiency or extinction of the beneficial intestinal microflora (avitaminosis or hypovitaminosis).

Daily vitamin K requirements is usually about 2 mg. Individual diet and bioavailability are the critical parameters to maintain proper level of vitamin K in a human body. Vitamin $K_1$ is poorly absorbed in humans (5-10%), and for the same reason synthetic MK-4 type of vitamin $K_2$ is recommended to be administered at large quantities and frequent doses. The numerous trials have evidenced that the highest biological activity of all vitamin K homologues has MK-7 type of vitamin $K_2$:

MK-7

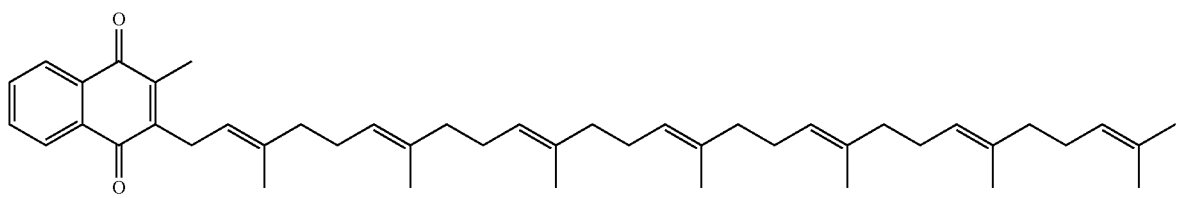

MK-7 type of vitamin $K_2$ is characterized by better bioavailability and efficacy than the other vitamins K. It is also characterized by the high absorption in small intestine and sustained presence in a blood serum (up to 3 days). Even small daily doses of vitamin MK-7 are sufficient to provide all cells and tissues with vitamin K dependent enzymes and proteins at the proper level. On account of participation in calcium metabolism, vitamin MK-7 is indirectly involved in strong bones formation. Unlike vitamin $K_1$, it also influences arterial vessel wall condition.

Vitamin MK-7 structure consists of naphthalenedione ring (menadione) with the attached alkyl chain comprising seven isoprene units (heptaprenyl), thus it contains seven double bounds of trans configuration. Considering its molecular structure, synthetic vitamin MK-7 could be synthesized from menadione or its protected derivative, menadiol, following one of the strategies mentioned below:
1. attachment of heptaprenyl chain directly to menadiol molecule, according to so called "0+7" strategy;
2. attachment of chain shorter fragments to monoprenyl derivative of menadiol, according to "1+n+m" strategy;
3. attachment of hexaprenyl chain to monoprenyl derivative of menadiol, according to "1+6" strategy.

U.S. Pat. No. 4,199,531 discloses the process for elongation of the side chain of menadiol derivative having at position C-3 from 1 to n terminal activated isoprenyl units, accomplished by its stereo- and regio-selective alkylation with activated side chain precursor consisting of m isoprenyl units. The carbanion generated under basic conditions on the carbon atom adjacent to arylthio, arylsulfinyl or arylsulfonyl terminal group of one substrate is subsequently alkylated with alkyl halide as the second substrate. Then, in case of the reaction of monoprenylmenadiol arylsulfonyl derivative with polyprenyl halide, the product is subjected to reductive desulfonylation, deprotection of the hydroxyl groups if there is a need thereof, and/or oxidation to afford menaquinone derivative. According to the specification, alkylation is performed under the basic conditions, in the presence of bases such as butyllithium or phenyllithium, under dry conditions; in a solvent such as tetrahydrofurane, ether or 1,2-dimethoxyethane; at −78° C. to 20° C. temperature range. Although the general chemical formula comprises the chemical structure of vitamin MK-7, no specific preparative example for this vitamin synthesis is given in the specification.

The above mentioned process for alkylation of phenylsulfonyl derivative of monoprenylmenadiol using triprenyl halide yielding vitamin MK-4 (according to "1+3 strategy") has been described in *J. Org. Chem.* 2003, 68, 7925. There has also been disclosed the synthesis of phenylsulfonyl derivative of monoprenyl menadiol dimethoxy-ether (MK-1) from menadiol.

In the International Patent Application WO 2011/117324, multi-step process for preparation of polyisoprenyl alcohols and halides having different length chains in Biellmann type reaction has been disclosed. The coupling reaction of arylsulfonyl or arylthiol polyisoprenyl derivative having p isoprenyl units (p=0-4) with the properly protected (for example with the acetyl groups) primary polyisoprenyl halide having q isoprenyl units (q=0-4) is carried out in the presence of a non-nucleophilic base. Subsequent removal of $SO_2Ar$ or SAr group under reductive conditions, followed by deprotection of hydroxyl group, furnishes the desired product. In Example 6, synthesis of pentaprenyl alcohol from diprenyl-alcohol bromide, having protected acetyl and phenylsulfonyltriprenyl groups, is described. After each step of the process: alkylation, desulfonylation and removal of hydroxyl protecting groups, purification of the product by silica gel flash chromatography is necessary. Polyprenyl halides obtained according to this procedure have been used in the vitamins $K_2$ synthesis, in particular vitamin MK-7 synthesis, under Grignard/Kumada or Suzuki conditions, following "0+7" or "2+5" strategy.

Publication WO 2010/03500 discloses the synthesis of vitamin $K_2$ that is based on the polyprenyl ring attachment to the protected activated menadiol derivative, under Grignard/Kumada or Suzuki conditions, according to "0+7 strategy".

In the two aforementioned International Patent Applications, the activated menadione derivative with carbonyl functions protected with alkyl or benzyl groups, as the potential synthetic substrate has been claimed. However, in the preparative examples only methoxy-derivatives of menadiol have been used.

The aim of the present invention was to develop the process for preparation of synthetic all-trans vitamin MK-7, in which easily available substrates could be used.

Moreover, the aim of the invention was to develop the process enabling the preparation of vitamin MK-7 characterized by high purity, which would meet the quality requirements approved for both the dietary supplements as well as active pharmaceutical ingredients.

The further aim of the present invention was to provide vitamin MK-7 of demanded purity in a high yield, in a process optimized to eliminate or reduce the troublesome and time-consuming multiple chromatographic purifications of all intermediates.

These goals have been achieved due to coupling of a hexaprenyl chain precursor of all-trans configuration with a menadiol derivative bearing the phenylsulfonyl monoprenyl terminal group and protected in the form of alkoxy-ethers, especially in the form of ethoxy-ether. Unexpectedly, it has appeared that this phenylsulfonyl monoprenyl menadiol ethoxy-derivative could be obtained in a crystalline form, that significantly improves the process of its purification. Low level of impurities accompanying this new derivative, enables preparation of all-trans configuration vitamin MK-7 of the high purity, with the limited necessity of purifications of intermediates by means of preparative chromatography.

DISCLOSURE OF THE INVENTION

The invention relates to the process for preparation of MK-7 type of vitamin $K_2$, represented by the formula (I), (I)

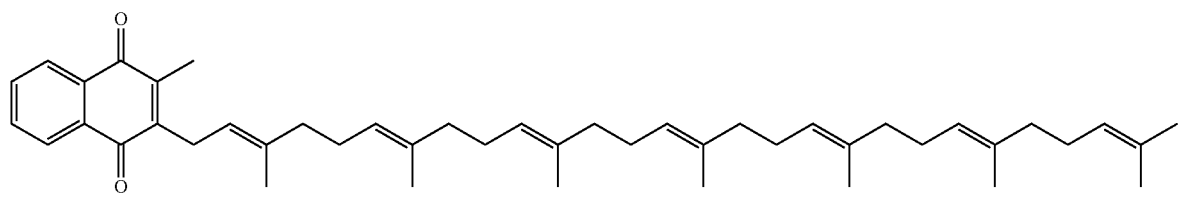

comprising the steps of:
(a) reacting an α-sulfonyl carbanion generated in situ from the phenylsulfone of monoprenylmenadiol derivative of formula (II)

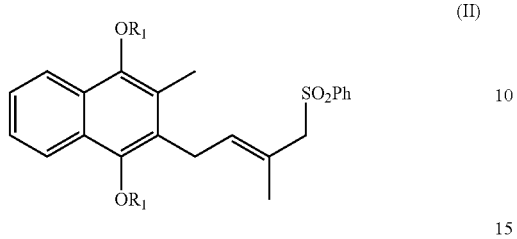

wherein $R_1$ represents $C_{1-3}$-alkyl,
in the presence of a strong organometallic base,
with a hexaprenyl halide of formula (VII)

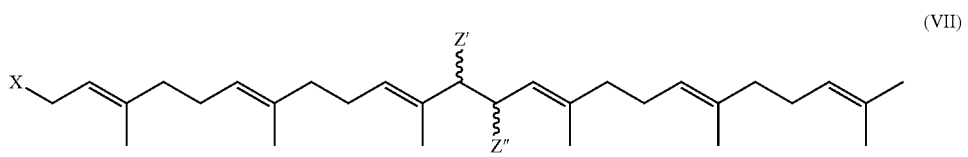

wherein
X represents halogen, preferably bromine,
Z' and Z" both represent H, or one of Z' and Z" is H and the other is phenylsulfonyl —SO$_2$Ph group, as an alkylating agent;
to yield the phenylsulfonyl derivative of menadiol of the formula (VIII)

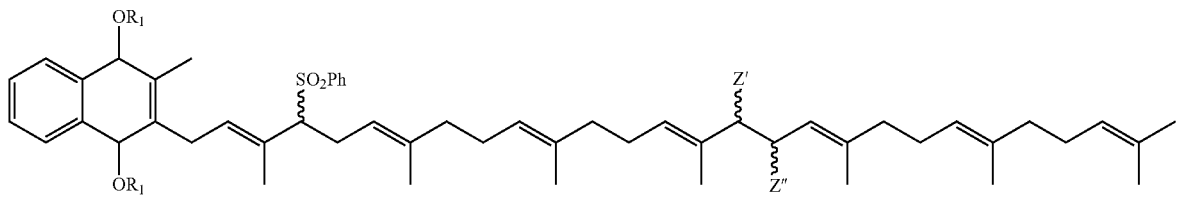

wherein $R_1$, Z' and Z" have the meaning defined above,
(b) removing the phenylsulfonyl groups from the menadiol derivative of formula (VIII) by the reductive elimination, to yield the menadiol derivative of formula (IX)

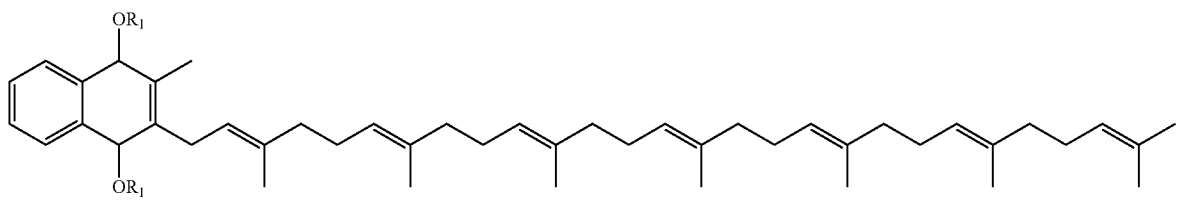

wherein $R_1$ has the meaning defined above;

(c) subjecting the menadiol derivative of formula (IX) to an oxidative deeterification, to yield the crude menadione compound of formula (I), (I)

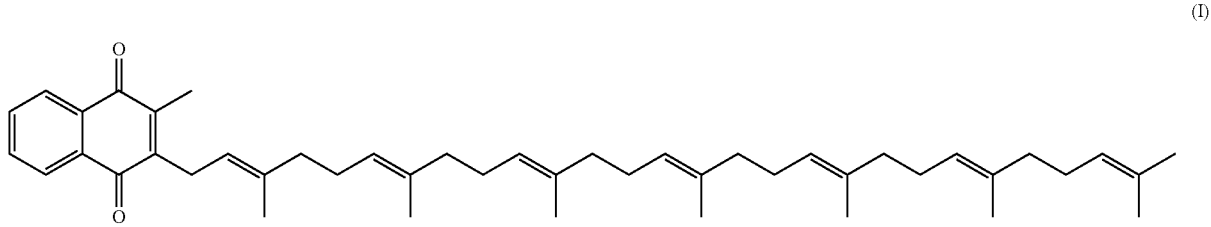 [SMILES: CC(C)=CCC/C(C)=C/CC/C(C)=C/CC/C(C)=C/CC/C(C)=C/CC/C(C)=C/CC/C(C)=C/CC1=C(C)C(=O)c2ccccc2C1=O]

(d) optionally, purifying the crude menadione compound of formula (I) to yield pure MK-7.

In the preferred variant of the invention, the hexaprenyl halide of formula (VII)

(VII)

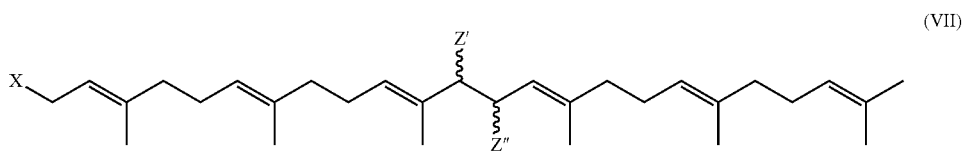

wherein
X represents halogen, preferably bromine,
Z' and Z" both represent H, or one of Z' and Z" is H and the other is phenylsulfonyl —SO$_2$Ph group,
used in step (a), is obtained in the process comprising the steps of:
(i) reacting two triprenyl fragments of formulae (III) and (IV)

(III)

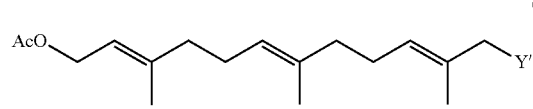

(IV)

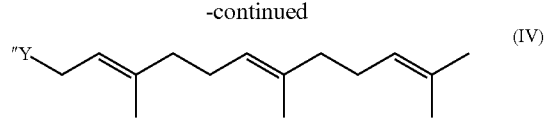

wherein:
if one of the Y' and Y" represents phenylsulfonyl —SO$_2$Ph group, then the other Y' or Y" represents the halogen atom,
in the presence of a strong base, to yield the compound of formula (V)

(V)

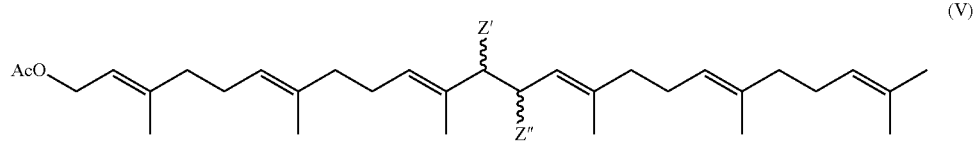

wherein one of Z' and Z" represents H and the other represents phenylsulfonyl —SO$_2$Ph group,
(ii) removing acetyl and, optionally, phenylsulfonyl groups from the compound of formula (V), to yield the hexaprenol derivative of formula (VI)

(VI)

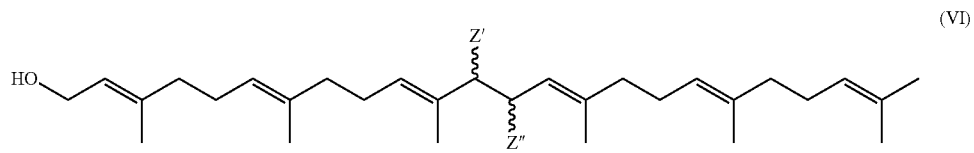

wherein Z' and Z" both represent H, or one of Z' and Z" represents H and the other represents phenylsulfonyl —SO$_2$Ph group, (iii) reacting the compound of formula (VI) with a halogenating agent, to yield the phenylosulfonyl-hexaprenyl halide of formula (VII)

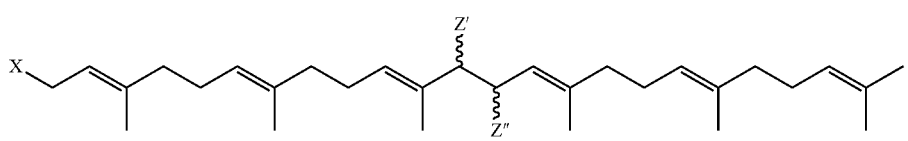

(VII)

wherein
X represents halogen atom, preferably bromine, and
Z' and Z" have the meaning defined above for the formula (VI),
(iv) optionally, The other aspects of the invention provide the new compounds used as the substrates and intermediates in the process for preparation of vitamin MK-7 according to the present invention, which are as follows:

1,4-diethoxy-2-methylnaphtalene,
1,4-dimethoxy-2-methyl-3-[(2E)-3-methyl-4-(phenylsulfonyl)-2-buten-1-yl]naphthalene,
the compounds of the general formula (VIII), wherein Z' and Z" both represent H, or one of Z' and Z" represents H, and the other represents phenylsulfonyl —SO$_2$Ph group, and
the compound of formula (IX), wherein R$_1$ is ethyl.

DETAILED DESCRIPTION OF THE INVENTION

In the process of the present invention, synthon A, represented by the formula (II), is the protected monoprenyl menadiol, having the terminal phenylsulfonyl function in allyl moiety attached in position C-3. Synthon A can be synthesized in a manner similar to that disclosed in the publication *J. Org. Chem.* 2003, 68, 7925-27, using commercially available menadione, which is first protected as dialkoxynaphthalene derivative, and than alkylated with (E)-4-chloro-2-methyl-1-phenylsulfonyl-2-buten under Friedel-Crafts conditions. Protection of hydroxyl groups prevents from the side reactions, in particular menadiol cyclization, which may occur under Friedel-Crafts conditions.

In the preferred embodiment of the invention, Synthon A is the monoprenyl derivative of menadiol, represented by the formula (II), wherein R$_1$ represents ethyl. Due to the presence of functionalized monoprenyl, the side chain in position C-3 can be elongated by coupling the appropriate number of isoprenyl units.

Menadiol protected with the ethoxy groups as well as the phenylsulfone of monoprenylmenadiol of formula (II), where R$_1$ represents ethyl, are the new compounds, which have not been reported in the literature. These two compounds, namely 1,4-diethoxy-2-methylnaphtalene and 1,4-dimethoxy-2-methyl-3-[(2E)-3-methyl-4-(phenylsulfonyl)-2-buten-1-yl]naphthalene, has been obtained in the crystalline forms. Therefore, they can be easily purified by crystallization, if necessary.

1,4-Diethoxy-2-methylnaphtalene shows the characteristic peaks in X-ray powder diffraction (XRPD) pattern recorded with CuKα, λ=1.54056 Å of relative intensities I/I$_0$>20% at the following reflection angles 2θ: 9.86 and 19.76±0.2°.

Figure 1:
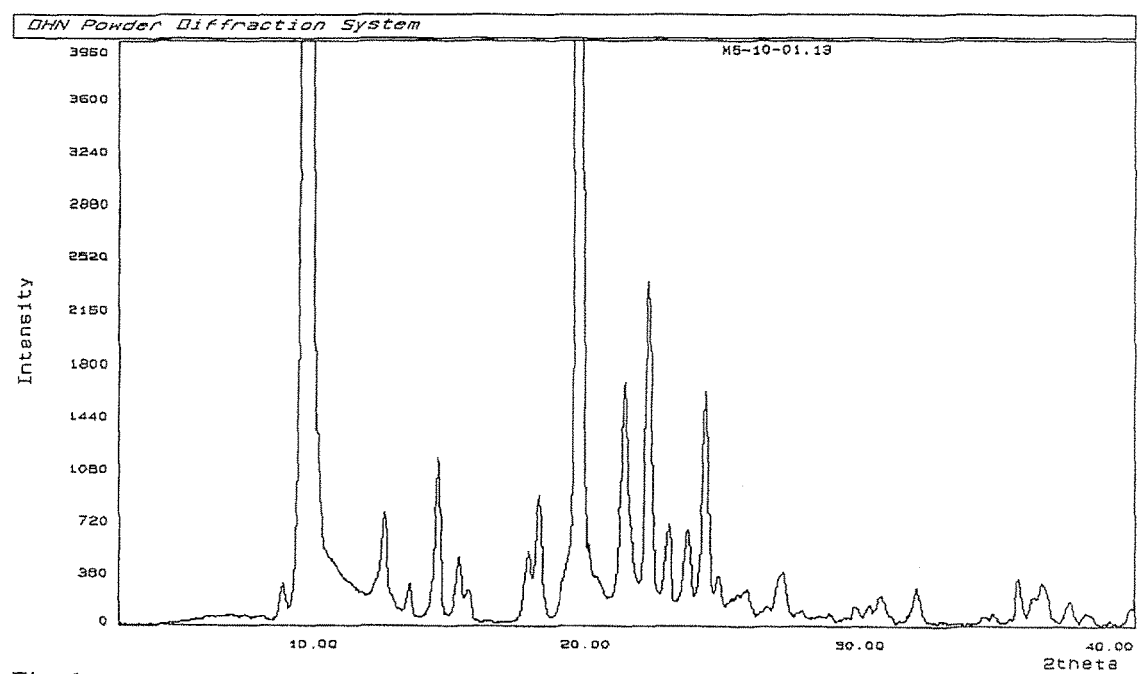
FIG. 1 shows the X-ray powder diffraction pattern of 1,4-diethoxy-2-methylnaphtalene which has the specific values of relative intensities I/I$_0$, reflection angles 2θ and interplanar spacing as shown in Table 1.

The X-ray powder diffraction pattern of 1,4-diethoxy-2-methylnaphtalene, has the specific values of relative intensities I/I$_0$, reflection angles 2θ and interplanar spacing, as presented on FIG. 1 and in the Table 1 below:

| d [Å] | 2θ [°] | I/I$_{max}$ [%] |
|---|---|---|
| 9.933 | 8.90 | 0.8 |
| 8.960 | 9.86 | 100 |
| 7.025 | 12.59 | 2.2 |
| 6.550 | 13.51 | 0.8 |
| 6.074 | 14.57 | 3.3 |
| 5.769 | 15.35 | 1.3 |
| 5.633 | 15.72 | 0.7 |
| 4.963 | 17.86 | 1.4 |
| 4.854 | 18.26 | 2.5 |
| 4.490 | 19.76 | 46.1 |
| 4.150 | 21.39 | 4.8 |
| 3.991 | 22.26 | 6.7 |
| 3.864 | 23.00 | 1.9 |
| 3.755 | 23.68 | 1.9 |
| 3.655 | 24.33 | 4.5 |
| 3.587 | 24.80 | 1 |
| 3.441 | 25.87 | 0.7 |
| 3.276 | 27.20 | 1 |

1,4-Dimethoxy-2-methyl-3-[(2E)-3-methyl-4-(phenylsulfonyl)-2-buten-1-yl]naphthalene, ie. compound of formula (II), wherein R$_1$=ethyl, shows the characteristic peaks in X-ray powder diffraction (XRPD) pattern recorded with CuKα, λ=1.54056 Å of relative intensities I/I$_0$>20% at the following reflection angles 2θ: 10.29, 12.69, 17.57, 19.62, 20.61, 21.05, 21.73, 23.25, 24.38 i 25.52±0.2°.

Figure 2:
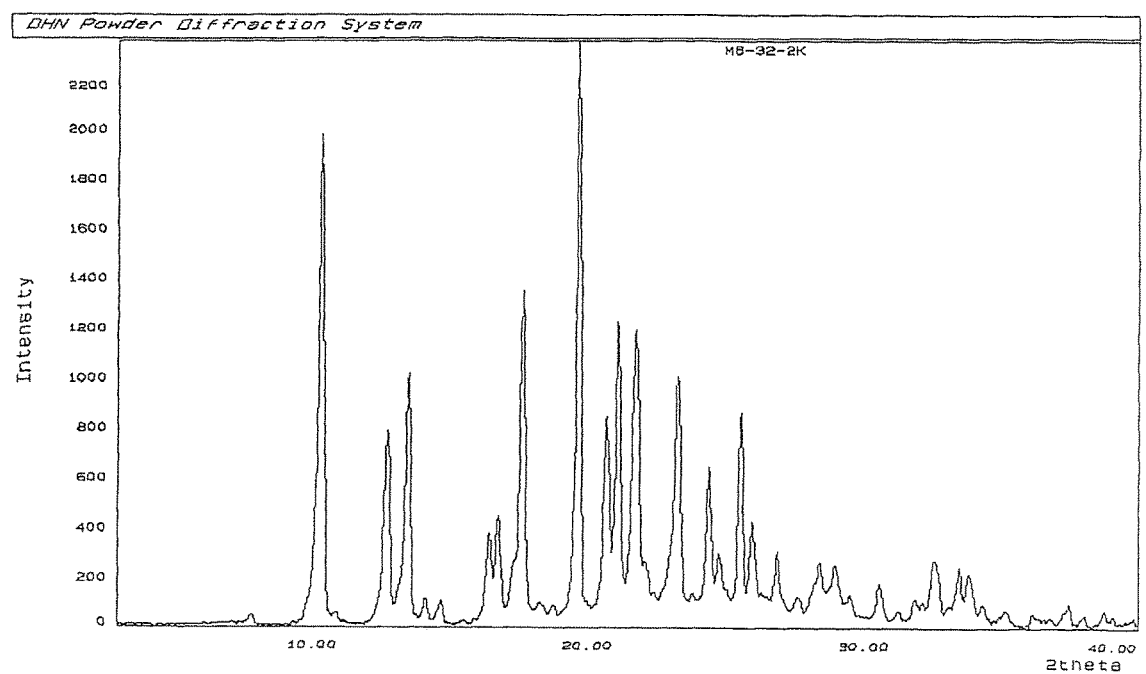
FIG. 2 shows the X-ray powder diffraction pattern of 1,4-dimethoxy-2-methyl-3[(2E)-3-methyl-4-(phenylsulfonyl)-2-buten-1-yl]napthalene which has specific values of relative intensities I/I$_0$, reflection angles 2θ and interplanar spacing as presented in Table 2.

The X-ray powder diffraction pattern of 1,4-dimethoxy-2-methyl-3-[(2E)-3-methyl-4-(phenylsulfonyl)-2-buten-1-yl]naphthalene, has the specific values of relative intensities I/I$_0$, reflection angles 2θ and interplanar spacing, as presented on FIG. 2 and in the Table 2 below:

| d [Å] | 2θ, [°] | I/I$_{max}$ [%] |
|---|---|---|
| 11.424 | 7.73 | 2 |
| 9.076 | 9.74 | 5 |
| 8.590 | 10.29 | 84 |
| 6.968 | 12.69 | 33 |

-continued

| d [Å] | 2θ, [°] | I/I$_{max}$, [%] |
|---|---|---|
| 6.292 | 14.06 | 5 |
| 6.049 | 14.63 | 5 |
| 5.410 | 16.37 | 16 |
| 5.303 | 16.70 | 19 |
| 5.141 | 17.23 | 11 |
| 5.044 | 17.57 | 57 |
| 4.883 | 18.15 | 4 |
| 4.521 | 19.62 | 100 |
| 4.305 | 20.61 | 36 |
| 4.217 | 21.05 | 52 |
| 4.087 | 21.73 | 50 |
| 4.023 | 22.08 | 11 |
| 3.823 | 23.25 | 42 |
| 3.648 | 24.38 | 27 |
| 3.487 | 25.52 | 37 |
| 3.432 | 25.94 | 18 |

Synthon B in the process of the present invention is hexaprenyl halide represented by the formula (VII), wherein Z' and Z" both represent hydrogen atoms, or one of Z' and Z" represents H and the other represents phenylsulfonyl group —SO$_2$Ph.

The key step in the preparation of vitamin MK-7 according to the present invention is coupling of the A and B synthons, accomplished due to the nucleophilic addition.

Coupling of A and B synthons in the alkylation reaction results in formation of vitamin K$_2$ derivative, possessing at least one phenylsulfonyl group in heptaprenyl chain and hydroxyl groups protected in the ether form. Upon phenylsulfonyl groups removal and restoring the menadione structure, the final MK-7 type of vitamin K$_2$ is obtained.

In the preferred embodiment of the invention, hexaprenyl halide of the formula (VII) is obtained from commercially available E,E-farnesol.

The synthesis of hexaprenyl halide of formula (VII) can be accomplished according to two synthetic approaches.

In the first step E,E-farnesol is acetylated, and the resulting E,E-farnesyl acetate is oxidized with the use of selenium dioxide to E,E,E-12-hydroxy-farnesyl acetate, as it is depicted in Scheme 1.

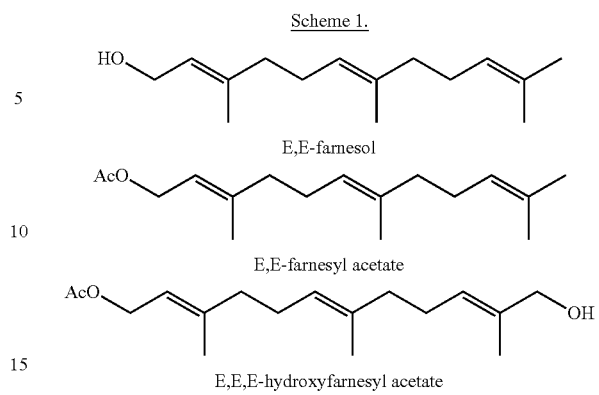

Scheme 1.

Selenium dioxide (SeO$_2$) mediated incorporation of oxygen atom at allylic position is known, for example, from T. Wirth et al., Organoselenium Chemistry, Modern Developments in Organic Synthesis, ed. Springer. According to the present invention, oxidation can be performed using stoichiometric amount of SeO$_2$, or preferably, catalytic amount of SeO$_2$ using acid as co-catalyst, for example salicylic acid or SiO$_2$, in presence of 2-3-fold molar excess of co-oxidizer, such as tert-butyl peroxide (in water or organic solvent) or hydrogen peroxide. In another embodiment of the invention, oxidation reaction can be accomplished using SeO$_2$ in the presence of molar excess of N-oxide N-methylmorpholine.

Then, according to the first variant of the synthesis, which is illustrated in Scheme 2, E,E,E-12-hydroxyfarnesyl acetate is converted into its phenylsulfonyl derivative (IIIA) in a two-step synthesis, via the bromide derivative, which is further treated with sodium benzenesulfinate. Phenylsulfonyl derivative of farnesyl acetate (IIIA) is coupled in the alkylation reaction with farnesyl halide (IVA), preferably farnesyl bromide, obtained in the reaction of E,E-farnesol with one of the commonly used halogenating agents.

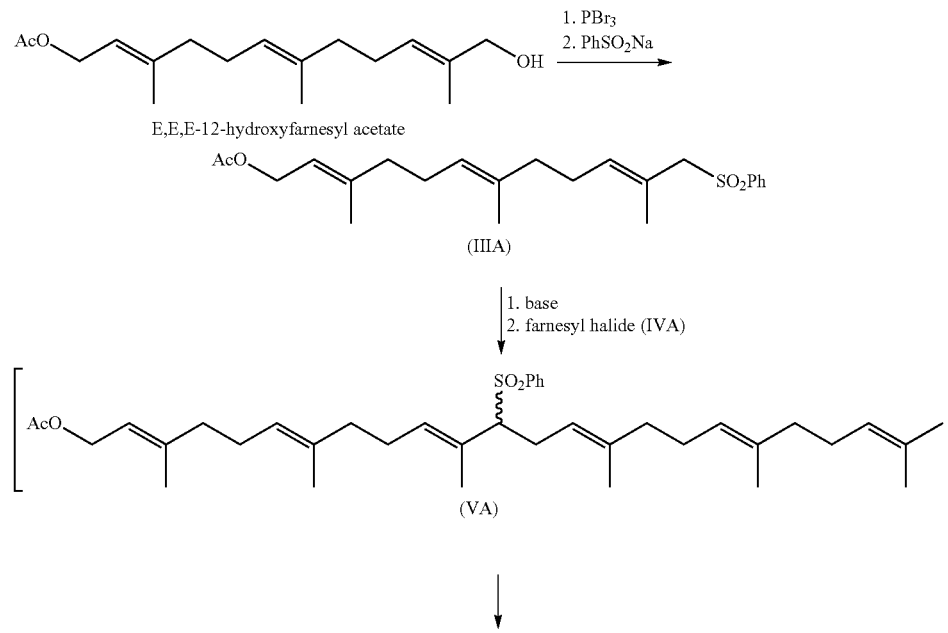

Scheme 2. Coupling of triprenyl fragments (first variant)

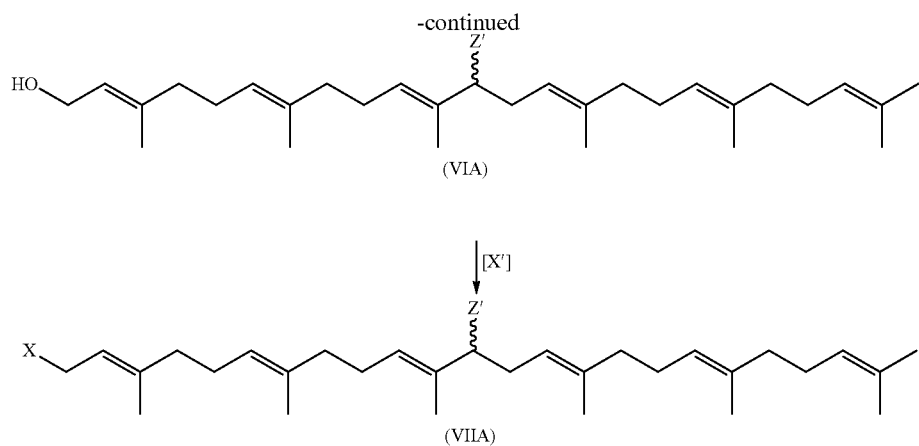
(VIA)
[X']
(VIIA)
According to the second variant of the synthesis (Scheme 3), E,E-farnesyl acetate is transformed into its halide (IIIB) (preferably bromide), which, in the same manner as in the first variant, is reacted with sulfone (IVB) obtained from farnesyl acetate, to obtain phenylsulfonyl derivative of hexaprenyl acetate (VB).
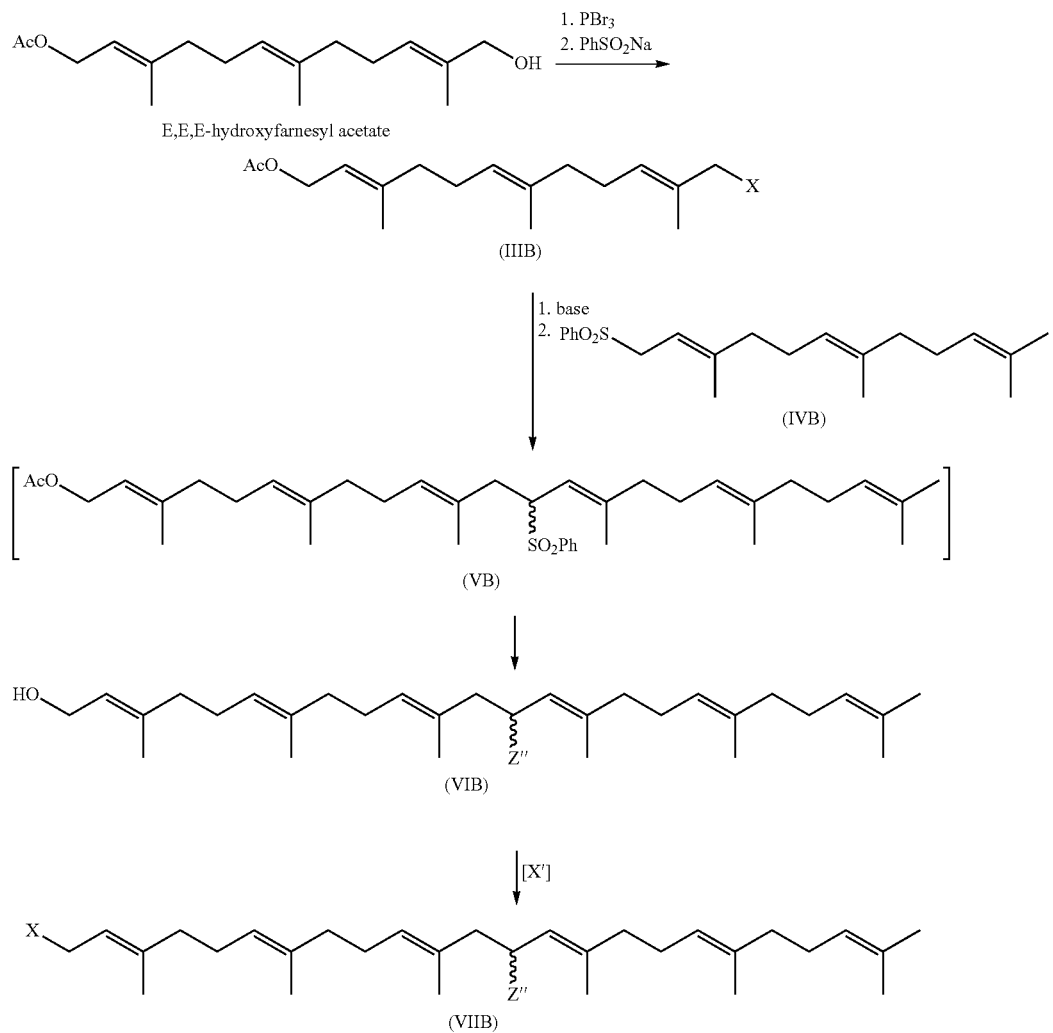

Coupling of polypropenyl chain fragments by way of alkylation of the proper sulfones is generally known in the art, among the others from *J. Org. Chem.* 2003, 68, 7925; *J. Chem. Soc. Perkin I* 1981, 761; *J. Org. Chem.* 2008, 73, 7197; *Tetrahedron* 2009, 65, 6310. This reaction can be performed in the presence of a strong base, such as potassium tert-butanolate, n-butyllithium, lithium, sodium or potassium bis(trimethylsilyl)amidate, in a polar aprotic solvent.

The phenylsulfonyl hexaprenyl acetate (VA) or (VB) is then transformed into the hexaprenol derivative of formula (VIA) or (VIB), respectively, wherein Z' or Z" in Schemes 2 and 3 independently represent phenylsulfonyl group $SO_2Ph$.

To obtain the hexaprenol derivative of formula (VIA) or (VIB), wherein Z' or Z" independently represent phenylsulfonyl group $SO_2Ph$, the acetyl group is removed upon the hydrolysis under the basic conditions, while the phenylsulfonyl group is left intact.

The processes of triprenyl fragments coupling and hydrolysis of the phenylsulfonyl hexaprenyl acetate (V) can be accomplished successively, following isolation and purification of the compound (V).

In the preferred embodiment of the invention, however, the steps of coupling of triprenyl chain fragments and further hydrolysis are carried out successively in an "one pot" reaction.

The resulting compound of formula (VI) wherein Z' or Z" independently represent phenylsulfonyl group $SO_2Ph$, can be subsequently converted into halide of the formula (VII), wherein Z', or Z" represent phenylsulfonyl group $SO_2Ph$, which can be used as Synthon B in further synthesis of MK-7 type of vitamin K.

Alternatively, the phenylsulfonyl groups can be removed from the phenylsulfonyl derivative of hexaprenyl of formula (VI), to obtain the compound of formula (VI), wherein Z' or Z" independently represent H.

The acetyl and phenylsulfonyl groups can be removed successively or simultaneously.

phenylphosphite type bidentate ligands of the formula $[M\{Ph_2P(CH_2)nPPh_2\}X_2]$, wherein n=2-5, X=Cl or Br and M=Co, Ni or Pd as catalysts.

Preferably, metal borohydride is used, unsubstituted or substituted, having up to three substituents selected among $C_{1-5}$-alkyl and phenyl, such as lithium triethylborohydride, lithium tri-sec-butylborohydride, tri-sec-butyllithium, sodium or potassium, potassium triphenylborohydride. Most preferably, lithium triethylborohydride in presence of $Pd(dppe)Cl_2$ complex, where dppe represents 1,2-bis(diphenylphosphino)ethane or $Pd(dppp)Cl_2$, where dppp represents 1,3-bis(diphenylphosphino)propane.

In the other embodiment of the present invention, acetyl and phenylsulfonyl groups of the compound of formula (V) are removed subsequently. In this case, the steps of triprenyl chain fragments coupling, acetyl group removal and phenylsulfonyl group reductive elimination preferably are carried out successively, in an "one-pot" reaction, without separation of the intermediates.

Then, in the reaction of compound of the formula (VI), wherein Z' or Z" independently represent H or phenylsulfonyl group, with halogenating agent, hexaprenyl halide of the formula (VIIA) or (VIIB), respectively, unsubstituted or substituted with phenylsulfonyl group in a side chain, is obtained in good yield.

Suitable halogenating agents are, for example, $SOCl_2$ or HCl (gaseous) converting the hexaprenol into the corresponding chloride, $PBr_3$ or HBr—into bromide and $PPh_3/I_2$, $PI_3$ or HI—into iodide.

Preferably, hexaprenol derivative of formula (VI) is converted into hexaprenyl bromide of formula (VII) in the reaction with $PBr_3$.

In the most preferred embodiment of the invention, the acetyl groups of the compound of the formula (V) are removed, the resulting hexaprenol derivative of the formula (VI), wherein one of Z' and Z" is H and the other is phenylsulfonyl —$SO_2Ph$ group, is reacted with the halogenating agent, and thus obtained halide of the formula (VII),

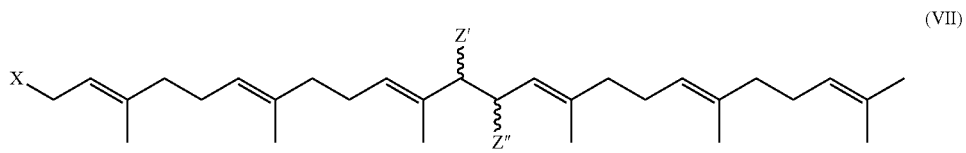

(VII)

wherein

X represents halogen, preferably bromine, one of Z' and Z" is H and the other is phenylsulfonyl —$SO_2Ph$ group, is used as Synthon B in the synthesis of MK-7 type of vitamin $K_2$.

For coupling with Synthon A, from menadiol derivative of the formula (II), α-sulfonyl carbanion is generated in situ in the presence of organometallic strong base. Formation of stable —CH—$SO_2$—Ar carbanions due to activation of (arylsulfonyl)methylene group under basic condition, was disclosed in some publications, among the others, P. E. Magnus, Tetrahedron 33 (1977), 2019; B. M. Trost, Bull. Chem. Soc. Jpn. 61 (1988), 107; N. S. Simpkins, Tetrahedron 46 (1990), 6951. To generate carbanions, bases such as n-butyllithium, potassium tert-butanolate, lithium or sodium bis(trimethylsilyl)amidate ($Me_3$-Si—N(M)-Si-$Me_3$, M=Li, Na, K) and lithium or sodium diisopropylamidate were used, as has been described in the publication by I. R. Baldwin, R.

The methods of removal of arylsulfonyl groups of substituted (arylsulfonyl)alkanes are known in the art. They can be removed under different reductive conditions, depending on molecular structure of the substrate (Y. Liu, Y. Zhang, Org. Prep. Proc. Int. 33 (2001), 372). Among general methods, reduction with alkali metals dissolved in liquid ammonia (for example J. R. Hwu at al., J. Org. Chem. 61 (1996), 1493-1499); reduction with Mg/MeOH or Mg/EtOH+$HgCl_2$ (G. H. Lee at al., Tetrahedron Lett. 34 (1993), 4541-2; A. C. Brown, L. A. Carpino, J. Org. Chem. 50 (1985), 1749-50) and also with sodium amalgam in MeOH, buffered with $Na_2HPO_4$ (B. M. Trost at al., Tetrahedron Lett. 17 (1976), 3477-8) should be mentioned.

In one embodiment of the present invention, acetyl and phenylsulfonyl groups of the compound of formula (V) are removed simultaneously, in the reaction of reductive elimination with borohydrides of alkali metals, such as sodium or potassium, using complexes of metal (II) dihalides with J. Whitby Chem. Commun. (2003), 2786-2787. Preferably, in the process according to the present invention, sulfonyl carbanion is generated using alkali metal bis(trimethylsilyl) amidates, most preferably, sodium bis(trimethylsilyl)amidate, owing to which high regio-selectivity and reaction yields are achieved. The reaction if carried out in a polar aprotic solvent, such as tetrahydrofuran, dimethylformamide, heksamethylphosphotriamide or the mixture thereof.

The obtained menadiol derivative of the formula (VIII) is isolated from the reaction mixture, or is used without isolation in the subsequent step of phenylsulfonyl group(s) removal.

Phenylsulfonyl groups can be removed under reductive elimination conditions, using borohydride of alkali metal, such as lithium, sodium or potassium, and catalyzed by complexes of metal (II) dihalides and bidentate ligands of phenylphosphite type of the formula [M{Ph$_2$P(CH$_2$) nPPh$_2$}X$_2$], wherein n=2-5, X=Cl or Br and M=Co, Ni or Pd, most preferably, lithium triethylborohydride with Pd(dppe)Cl$_2$ complex, wherein dppe represents 1,2-bis(diphenylphosphino)ethane or Pd(dppp)Cl$_2$, wherein dppp represents 1,3-bis(diphenylphosphino)propane.

In the last step of synthesis the compound of the formula (IX) is subjected to oxidative deeteryfication, to restore the quinine structure of the starting menadione.

Oxidation of the phenolic groups to the quinone structures could be typically accomplished by use of one of the common oxidizing agents, such as chromium trioxide in acetic acid, sodium dichromate or Fremy's salt, ie. potassium nitrosodisulfonate.

In the preferred embodiment of the present invention, cerium ammonium nitrate (CAN) is used as the oxidizing agent. CAN is known, for example, from *J. Org. Chem.* 2003, 68, 7925-27.

The crude MK-7 type of vitamin K$_2$ product (I) obtained in the process of the invention could be isolated, for example by column chromatography, and then it may be purified, for example by high performance liquid chromatography, and/or by crystallization.

The process for preparation of MK-7 type of vitamin K$_2$ of to the present invention, performed according to "1+6" strategy, enables preparation of MK-7 type of vitamin K$_2$ using easily available starting compounds, providing the desired all-trans configuration of double bonds that conforms with the configuration of the A and B synthons.

In the preferred embodiment of the process according to the present invention, α-sulfonyl carbanion of monoprenyl menadiol of the formula (II) is alkylated with hexaprenyl halide of the formula (VII), wherein X represents halogen atom (fluorine, chlorine, bromine or iodine), preferably bromine, and Z' or Z" independently represents phenylsulfonyl group —SO$_2$Ph. Subsequently, all phenylsulfonyl groups are simultaneously removed from the resulting diphenylsulfonyl derivative of menadiol of the formula (VIII). Due to this approach, vitamin MK-7 is obtained in unexpectedly high yield and in one step shorter process, which effects in reduction of time and expensive reagents consumption. Moreover, the total amount of both "migration-type" (ie. formed as a result of the double bonds migration along the heptaprenyl chain) and "cis" impurities, which tends to be formed in desulfonation step, could be substantially reduced.

The present invention provides simplified and shorter process affording vitamin K$_2$ in comparison to the methods reported in the literature up to now, in particular those disclosed in U.S. Pat. No. 4,199,531 and WO 2011/117324. Regardless elimination of some intermediates separation and purification steps, the described process furnishes vitamin MK-7 of purity which meets the requirements for dietary supplements and active pharmaceutical ingredients.

In particular, the protection of phenylsulfonyl derivative of monoprenyl menadiol in form of the ethoxy-ether groups simplifies purification of the crystalline synthon A and enables synthesis of vitamin MK-7 bearing all-trans configuration, eliminating expensive and troublesome chromatographic purification of the final product.

The present invention is illustrated by the following examples.

EXAMPLES $^1$H NMR, $^{13}$C NMR and DEPT spectra were recorded on Varian Gemini-2000 (200 and 50 MHz) NMR spectrometer in CDCl$_3$. Spectra were referenced internally using the residual solvent resonances and reported in ppm relative to TMS signal (0.00 ppm for $^1$H NMR) and the residual signal of CDCl$_3$ (77.00 ppm for $^{13}$C NMR).

Example 1

Menadiol

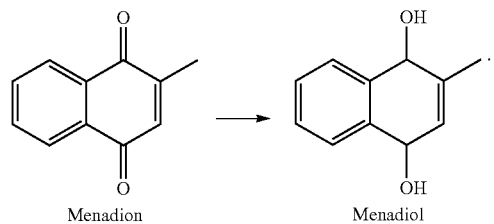

Menadion        Menadiol

Sodium dithionate (85%, 600 g, 2.93 mol) was dissolved in water (2.6 L). In a reaction vessel of 10 L capacity, menadione (234 g, 1.36 mol) was suspended in ethyl acetate (3.2 L) and stirred under nitrogen to make solution uniform. Sodium dithionate solution was transferred into the reaction vessel and the resulting mixture was vigorously stirred for 10 min. until the solution became yellow. The layers were separated, water phase was discarded, organic phase was washed with water (1×2 L) and brine (1×2 L). The solution was transferred into a round bottom flask. Solvent was removed under reduced pressure to dryness (using high vacuum in the end). The solid was obtained in 248 g yield (calc. yield 236.74 g). The solid was treated with toluene (1.140 L), the solution was condensed up to ⅔ of the initial volume (total volume of removed toluene was about 460 mL). Obtained suspension (about 900 mL) was used in the next step.

Example 2

Diethoxymenadiol

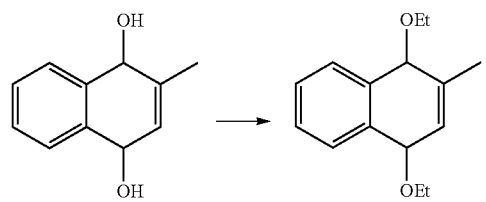 [SMILES: CC1=CC(O)c2ccccc2C1O ; CCOC1C=C(C)C(OCC)c2ccccc21]

The suspension obtained in Example 1 was placed in a reaction vessel of 20 L capacity, equipped with thermocouple, $N_2$ line adapter, azeotropic condenser, heating mantle and magnetic stirrer. To this solution toluene (5.5 L), 18-crown-6 ether (0.77 g) were added. $K_2CO_3$ (1800 g) and diethyl sulphate (1550 mL) were added while stirring. The resulting mixture was refluxed (~110° C.) for 2 h. Heating was stopped and the mixture was left overnight with slowly stirring. Water (7 L) was poured into the reaction vessel, and the mixture was refluxed (85° C.) for 1.5 h. Solution was cooled down to RT, then transferred into a separatory funnel. Water phase was discarded, organic layer was washed with water (2 L) and water-brine mixture (2 L, 1:1). Organic phase was separated and evaporated to dryness (high vacuum in the end of evaporation). The product was obtained in 680 g yield (calc. yield 689 g)

Column Chromatography

The obtained product was purified by column chromatography on silica gel ($m_{diethoxymenadiol}$=680 g; $m_{SiO2}$=2650 g; F=4, $V_K$=4.4 L, $V_F$=4.4 L). The silica gel bed was suspended in hexane (8 L). Before placing on a column, the reaction product was dissolved in hot hexane (1:2.5) in 2.5 L total volume. Silica gel bed was washed with hexane (4.4 L), then with the mixture of hexane:toluene (1:1) 5×4.4 L. 3.5 L of eluate, which was pure hexane fraction, was collected and 6 fractions were collected separately: one hexane fraction and 5 fractions after washing column bed with the mixture of hexane:toluene. The last fraction (6) was discarded, it contained trace amounts of the product (TLC), from 1-5 fractions solvents were removed, affording 665.3 g of white solid. Yield 96.56%.

M.p. 57.91° C. (DSC);

$^1$H NMR (CDCl$_3$), δ (ppm): 1.50 (6H, m), 2.42 (3H, s), 3.97 (2H, k), 4.14 (2H, k (7.9 Hz)), 7.34-7.54 (2H, m), 7.76-7.86 (1H, m), 8.16-8.28 (1H, m);

$^{13}$C NMR (CDCl$_3$), δ (ppm): 14.90 (CH$_3$), 15.80 (CH$_3$), 16.51 (CH$_3$), 63.82 (CH$_2$), 69.32 (CH$_2$), 107.71 (CH), 121.57 (CH), 122.23 (CH), 124.36 (CH), 125.32 (C), 125.73 (C), 126.23 (CH), 129.01 (C), 145.92 (C), 150.74 (C).

Example 3

Phenylsulfone of Monoprenyl Menadiol

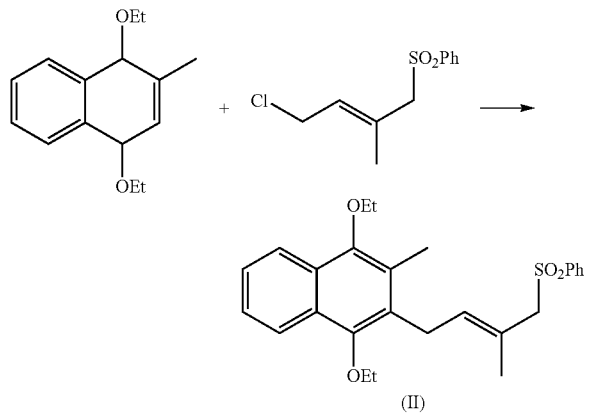

In a reaction vessel of 1.5 L capacity, equipped with septum, water condenser with CaCl$_2$ tube, thermocouple, magnetic stirrer, nitrogen line adapter, immersed in a cooling bath (acetone/CO$_2$), diethoxymenadiol (75 g, 325 mol) and phenylsulfone (100 g, 0.407 mol) in 300 ml of methylene chloride were placed. The mixture was cooled to 0° C. and SnCl$_4$ (50 ml, 0.107 mol) was added dropwise through septum. During reagent addition (5 min), temperature was maintained at about 10° C. A cooling bath was removed and the reaction mixture was warmed to RT (20° C.) and stirred for 1 h. The solution was cooled down to 0° C. After water (380 mL) addition the mixture was transferred into a separatory funnel. Phases were separated, organic layer was washed with 5% brine (380 mL), the solution was condensed to dryness under reduced pressure. Two portions of ethyl acetate (180 mL) were added, each time the solvent was entirely removed to dryness (684 g). Obtained oily residue was dissolved in ethyl acetate (380 mL), the suspension was filtered through celite, which was washed with ethyl acetate (500 ml). The filtrate was condensed to dryness under vacuum in a round bottom flask. The oily product was obtained in 168.5 g yield (calc. yield 142.8 g).

The product was purified by column chromatography ($m_{M4}$=168.5 g; $m_{SiO2}$=1080 g; F=6.4; $V_k$=1.8 L, $V_k$=900 ml). The compound was placed on column bed in toluene. Separation was performed in the eluents gradient: hexane:ethyl acetate—9:1 (3.6 L), hexane:ethyl acetate—4:1 (7.2 L), hexane:ethyl acetate—2:1 (7.2 L), hexane:ethyl acetate—1:1 (80 ml). 20 Flasks were collected, each contained 3.75 L. The main product was found in 5b-7a fractions (280 g, oil).

Crystallization 1

The reaction product dissolved in hot, anhydrous EtOH (660 mL) was filtered and washed with anhydrous EtOH (100 mL). After EtOH (500 mL) and water (140 mL) addition, the mixture was stirred at RT for 24 h. The solid was filtered off and washed with cold (−25° C.) 90% EtOH (100 mL). It was air dried for 2 h and under vacuum for another 2 h. 147.34 g (25.73%) of white crystalline powder was obtained.

M.p. 102.73° C. (DSC);

$^1$H NMR (CDCl$_3$), δ (ppm): 1.50 (6H, m), 1.99 (3H, d), 2.19 (3H, s), 3.47 (2H, d), 3.72 (2H, s), 3.80-4.00 (4H, m), 5.00 (1H, t), 7.20-7.36 (3H, m), 7.36-7.50 (2H, m), 7.68-7.78 (2H, m), 7.92-8.08 (2H, m);

$^{13}$C NMR (CDCl$_3$), δ (ppm): 12.70 (CH$_3$), 15.75 (CH$_3$), 15.87 (CH$_3$), 17.04 (CH$_3$), 26.82 (CH$_2$), 65.92 (CH$_2$), 69.50 (CH$_2$), 70.27 (CH$_2$), 122.16 (CH), 122.23 (CH), 123.73 (C), 125.20 (CH), 125.45 (CH), 126.32 (C), 127.34 (C), 127.91 (C), 128.20 (2× CH), 128.71 (2× CH), 128.77 (C), 133.24 (CH), 134.41 (CH), 138.06 (C), 148.76 (C), 149.11 (C).

Example 4

E,E-Farnesyl Acetate

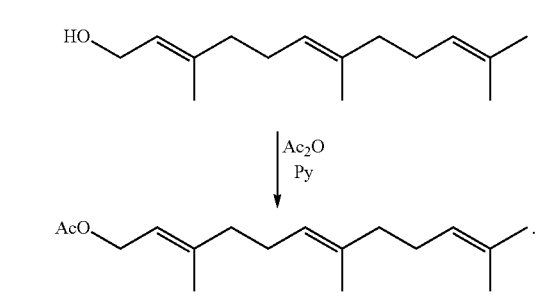

To the solution of E,E-farnesol (5.0 g, 22 mmol) in anhydrous pyridine (20 mL), acetyl anhydride was added (10 mL) at 0° C. under argon atmosphere. The reaction mixture was stirred at RT for 12 h. After completion of the reaction, the solution was poured into mixture of water and ice (40 mL) and the product was extracted with ethyl acetate (3×20 mL). Combined organic extracts were washed with saturated aqueous solution of $NaHCO_3$, brine and water. Organic layer was dried over anhydrous $Na_2SO_4$, filtered and evaporated to dryness. E,E-Farnesyl acetate was purified by column chromatography using ethyl acetate/hexane (2:98) as eluent to obtain pale yellow oil (5.62 g, 21 mmol, 95%).

Analytical results were in compliance with the literature data [*Biorg. Med. Chem.* 2008, 16, 3108]:

$R_f$=0.70 (hexane/ethyl acetate, 7:2);

$^1$H NMR ($CDCl_3$), δ (ppm): 5.33-5.36 (m, 1H), 5.08-5.11 (m, 2H), 4.59 (d, J=7.0 Hz, 2H), 1.96-2.13 (m, 8H), 1.71 (s, 3H), 1.68 (s, 3H), 1.60 (s, 3H);

$^{13}$C NMR ($CDCl_3$), δ (ppm): 171.0, 142.2, 135.4, 131.2, 124.3, 123.6, 118.3, 61.3, 39.6, 39.5, 26.7, 26.1, 25.6, 21.0, 17.6, 16.4, 15.9.

Example 5

E,E,E-12-Hydroxyfarnesyl Acetate

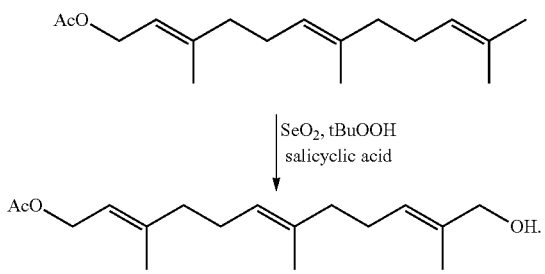

To the suspension of $SeO_2$ (210 mg, 1.89 mmol) and salicylic acid (261 mg, 1.89 mmol) in anhydrous $CH_2Cl_2$ (50 mL), the solution of tert-butyl hydroperoxide in water (70%, 9.40 mL) was added and stirring was continued at RT. After 30 min. the mixture was cooled down to 0° C. and the solution of E,E-farnesyl acetate (5.0 g, 18.9 mmol) in anhydrous $CH_2Cl_2$ (5 mL) was added dropwise. The resulting mixture was stirred at 0° C. for 5 min., then at RT for 24 h. The solvent was removed under vacuum, the residue was dissolved in $Et_2O$ (50 mL). The organic phase was washed with saturated aqueous $Na_2S_2O_3$ solution, water and brine, dried over anhydrous $Na_2SO_4$, filtered and evaporated to dryness under vacuum. The oily residue was dissolved in the mixture of methanol/THF (42 mL, 1:20), the solution was cooled to −10° C. and at this temperature $NaBH_4$ (0.15 g, 40 mmol) was added portionwise within 15 min. After 30 min. cold, saturated aqueous $NH_4Cl$ (50 mL) solution was added and the product was extracted with $CH_2Cl_2$ (3×50 mL). Combined organic extracts were washed with water and brine, dried over anhydrous $Na_2SO_4$, filtered and evaporated to dryness. The residue was purified by column chromatography, using hexane/AcOEt (88:12), to yield E,E,E-12-hydroxyfarnesyl acetate (oil, 2.11 g, 7.52 mmol, 40%)

$R_f$=0.27 (hexane/ethyl acetate, 7:2);

$^1$H NMR ($CDCl_3$), δ (ppm): 5.33-5.41 (2H, m), 5.09-5.12 (1H, m), 4.59 (2H, d, J=7.1 Hz), 3.99 (2H, bs), 2.05 (3H, s), 2.00-2.16 (8H, m), 1.71 (3H, s), 1.67 (3H, s), 1.60 (3H, s);

$^{13}$C NMR ($CDCl_3$), δ (ppm): 171.1, 142.2, 135.1, 134.7, 125.9, 123.9, 118.3, 68.9, 61.4, 39.4, 39.2, 26.1, 26.1, 21.0, 16.4, 16.0, 13.7.

Example 6

Triprenyl Sulfone (IIIA)

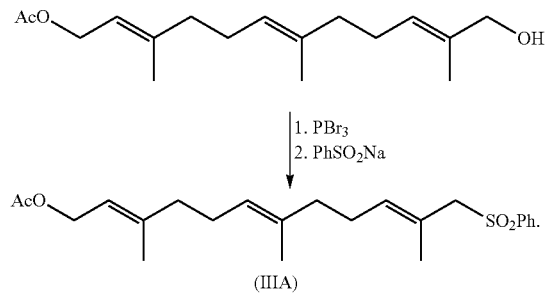

To the solution of E,E,E-12-hydroxyfarnesyl acetate (1 g, 3.57 mmol) in anhydrous THF (5 mL), $PBr_3$ (0.2 mL, 2.13 mmol) was added at 0° C. under argon atmosphere. After 3 h reaction was quenched by pouring the mixture into water and ice (10 mL). The organic phase was separated, the water layer was extracted with ether (3×10 mL). Combined organic extracts were washed with saturated aqueous $NaHCO_3$ solution and brine, dried over anhydrous $Na_2SO_4$, filtered and evaporated under vacuum. The product was obtained as colorless oil (1.1 g, 3.2 mmol, 90%).

The crude product (1.1 g, 3.20 mmol) was dissolved in anhydrous DMF (25 mL), then sodium benzenesulphate (1.05 g, 42 mmol) was added. The resulting suspension was stirred in dark, at RT for 18 h. Reaction was quenched by pouring the mixture into water (50 mL). The organic layer was separated, the water phase was extracted with ethyl acetate (3×25 mL). Combined organic extracts were washed with water and brine, then dried over anhydrous $Na_2SO_4$ and filtered. Solvent was removed under vacuum at 40° C. The crude product was purified by "flash" column chromatography, using heptane/ethyl acetate (7:2), to yield colorless oily sulfone (IIIA) in 1.138 g (79%) yield after 2 step reaction.

$R_f$=0.41 (hexane/ethyl acetate, 7:2);

$^1$H NMR ($CDCl_3$), δ (ppm): 7.84-7.86 (2H, m), 7.62-7.66 (1H, m), 7.52-7.56 (2H, m), 5.31-5.35 (2H, m), 4.99-5.07 (1H, m), 4.58 (2H, d, J=7.1 Hz), 3.72 (2H, bs), 2.05 (3H, s), 2.01-2.01 (8H, m), 1.76 (3H, s), 1.70 (3H, s), 1.54 (3H, s);

$^{13}$C NMR ($CDCl_3$), δ (ppm): 171.1, 142.0, 138.5, 136.0, 134.6, 133.3, 128.8, 128.5, 124.1, 123.2, 118.3, 66.2, 61.3, 39.4, 38.5, 26.9, 26.1, 21.0, 16.7, 16.4, 15.9.

Example 7

Triprenyl Sulfone (IIIB)

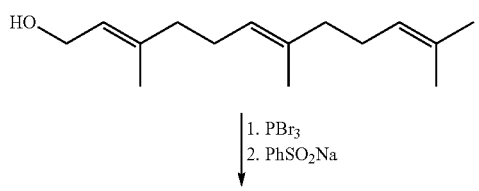

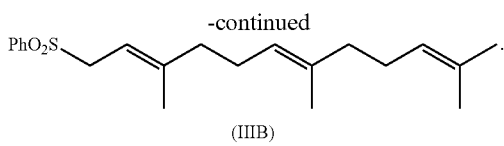

(IIIB)

To the solution of E,E-farnesol (1 g, 4.50 mmol) in anhydrous THF, PBr$_3$ (0.21 mL, 0.61 g, 2.25 mmol) was added dropwise at 0° C., the resulting mixture was stirred at 0° C. for 3 h. Reaction was quenched by addition of water and ice. The organic layer was separated, water phase was extracted with ether (3×10 mL). Combined organic extracts were washed with saturated aqueous NaHCO$_3$ solution and brine, dried over anhydrous Na$_2$SO$_4$, filtered and evaporated under vacuum to furnish bromide as colorless oil (2.2 g, 6.41 mmol, 90%). Crude product was dissolved in anhydrous DMF (5 mL) and PhSO$_2$Na (2.1 g, 12.82 mmol) was added, the solution was stirred in dark, at RT for 18 h. The reaction mixture was poured into water (15 mL), organic phase was separated, water layer was extracted with ethyl acetate (3×10 mL). Combined organic extracts were washed with water and brine, dried over anhydrous Na$_2$SO$_4$ and filtered. The solvent was evaporated under vacuum at 40° C. Crude product was purified by "flash" column chromatography, using heptane/ethyl acetate (95:5) as eluent. Triprenyl sulfone (IIIB) was obtained as colorless oil, in 1.23 g (79%) yield.

$R_f$=0.53 (hexane/ethyl acetate, 7:2);

$^1$H NMR (CDCl$_3$), δ (ppm): 7.89-7.86 (m, 2H), 7.66-7.62 (m, 1H), 7.56-7.52 (m, 2H), 5.20 (t, J=7.9 Hz, 1H), 5.10-5.04 (m, 2H), 3.81 (d, J=8.0 Hz, 2H), 2.07-1.96 (m, 8H), 2.01 (s, 3H), 1.68 (s, 3H), 1.60 (s, 6H), 1.32 (s, 3H);

$^{13}$C NMR (CDCl$_3$), δ (ppm): 146.4, 138.7, 135.7, 133.5, 131.4, 128.9, 128.5, 124.2, 123.3, 110.3, 56.1, 39.7, 39.7, 26.7, 26.2, 25.7, 17.7, 16.2, 16.0.

Example 8

12-Phenylsulfonyl Hexaprenyl (Variant I)

Compound (IIIA) (5.2 g, 12.9 mmol) was dissolved in 50 mL of the mixture of anhydrous THF/DMF (4:1). The solution was cooled down to −78° C. (dry ice/MeOH) and t-BuOK (1.594 g, 14.2 mmol) in anhydrous THF, was added dropwise (10 min.). The resulting yellow mixture was stirred at −78° C. for 2.5 h, then E,E-farnesyl bromide (IVA, 3.158 g, 14.2 mmol) in anhydrous THF was added. Stirring was continued at the same temperature for 4-5 h and the solution was left overnight to warm up to RT. The mixture was poured into saturated NH$_4$Cl solution (100 mL). Organic phase was separated and water layer was extracted with ether (3×10 mL). Combined organic extracts were washed with brine, dried over anhydrous Na$_2$SO$_4$, filtered and evaporated under reduced pressure. The crude product was dissolved in methanol (20 mL), 1M NaOH aqueous solution was added to reach pH 12 and the mixture was stirred at RT for 1 h. After evaporation on vacuo, the residue was poured into water and the product was extracted with diethyl ether (3×100 mL). The resulting compound (VIA) was separated from the crude mixture by column chromatography, using heptane/ethyl acetate (7:2). The oily title product was obtained in 3.5 g yield (6.17 mmol, 48%).

$^1$H NMR (CDCl$_3$), δ (ppm): 7.82-7.80 (m, 2H), 7.61-7.51 (m, 3H), 5.42-5.38 (m, 1H), 5.09-4.99 (m, 4H), 4.90-4.86 (m, 1H), 4.16 (d, J=6.9 Hz, 2H), 3.47 (dd, J=11.6, 3.9 Hz, 1H), 2.77 (m, 1H), 2.62-2.61 (m, 1H), 2.08-1.92 (m, 14H), 1.93 (m, 2H), 1.67 (s, 6H), 1.64 (s, 6H), 1.58 (s, 3H), 1.56 (s, 3H), 1.52 (s, 3H);

$^{13}$C NMR (CDCl$_3$), δ (ppm): 140.0, 138.4, 138.2, 135.7, 135.2, 134.7, 133.3, 128.8 (×4), 126.6, 124.3, 124.1, 123.8, 123.4, 118.8, 74.1, 59.4, 39.7, 39.7, 39.4, 38.6, 26.8, 26.5, 26.3, 25.7, 24.1, 17.7, 16.3, 16.0, 16.9, 13.8.

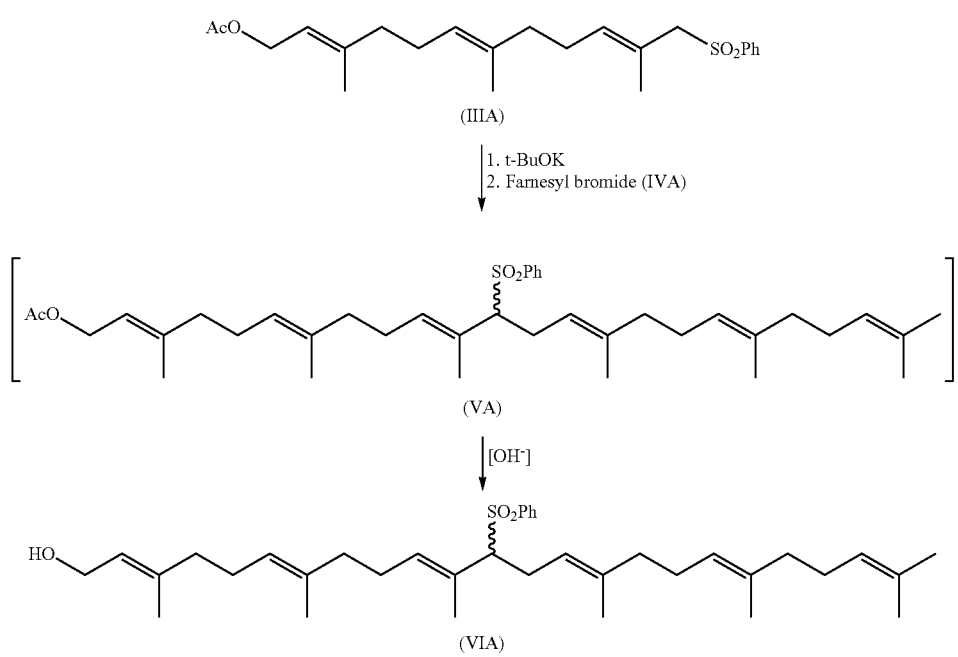

Example 9

13-Phenylsulfonyl Hexaprenyl (Variant II)

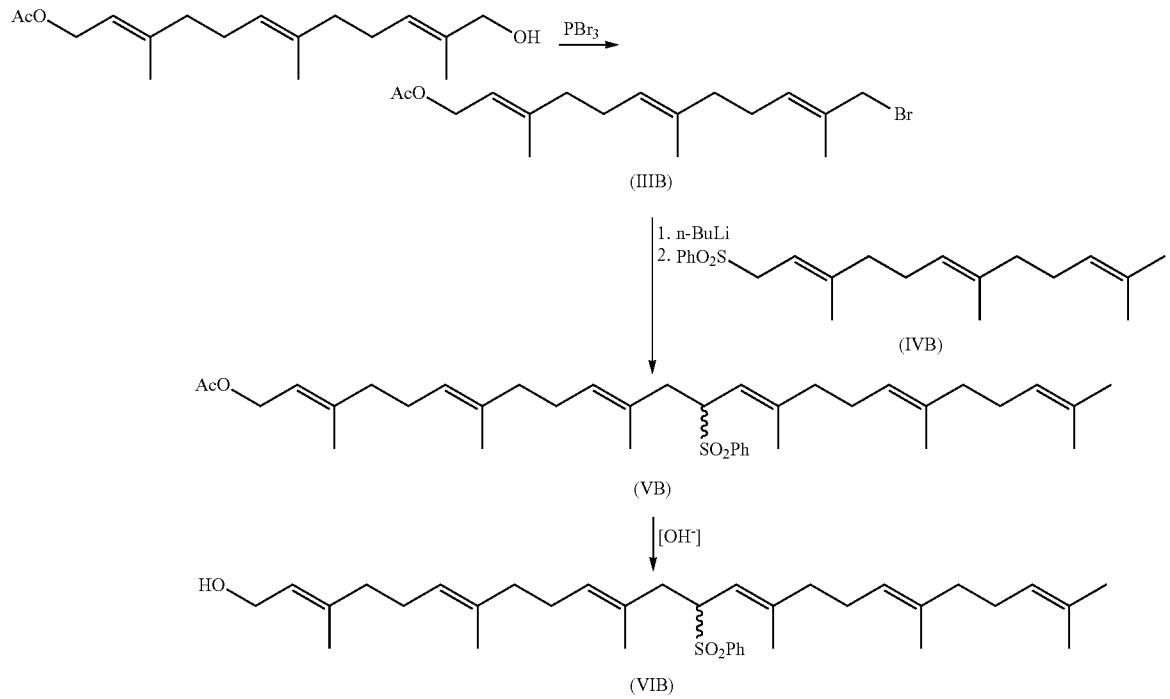

E,E,E-12-Hydroxyfarnesyl (1 g, 3.56 mmol) in anhydrous THF (5 mL) was treated with PBr$_3$ (0.17 mL, 1.78 mmol), at 0° C. under argon atmosphere. After 3 h reaction was quenched with cold water (10 mL). Organic layer was separated, water phase was extracted with ether (3×10 mL). Combined organic extracts were washed with saturated NaHCO$_3$ solution and brine, dried over anhydrous Na$_2$SO$_4$, filtered and evaporated under reduced pressure to yield bromide (IIIB), as colorless oil (0.98 g, 2.85 mmol, 80%). The crude product was used in the next step without purification.

To sulfone (IVB) (1.09 g, 3.14 mmol) dissolved in the mixture of anhydrous solvents THF/HMPA (15 mL, 4:1), cooled to −78° C. (dry ice/MeOH), the solution of nBuLi in hexane (2.0 mL, 3.14 mmol, 1.6 M), was added in 30 min. The resulting orange mixture was stirred at −78° C. for 1.5 h. The solution of bromide (IIIB) (0.98 g, 2.85 mmol) in 5 mL of anhydrous THF was added in 30 min. After 5 h cooling bath was removed, the mixture was left to reach 0° C. and saturated NH$_4$Cl (10 mL) solution was added. Phases were separated and water layer was extracted with ether (3×10 mL). Combined organic extracts were washed with brine, dried over anhydrous Na$_2$SO$_4$, filtered and evaporated under reduced pressure. The crude product was dissolved in dry methanol (10 mL), catalytic amount of sodium methanolate was added and the reaction mixture was stirred at RT for 2 h. After solvent evaporation under vacuum, the title product (VIB) was separated by column chromatography in hexane/ethyl acetate (75:25). Yield 0.84 g, (1.39 mmol, 39% after three steps).

$^1$H NMR (CDCl$_3$), δ (ppm): 7.86-7.84 (m, 2H), 7.62-7.50 (m, 3H), 5.44-5.40 (m, 1 H), 5.17-5.05 (m, 4H) 4.93 (d, J=10.4, 1H), 4.17 (d, J=6.9 Hz, 2H), 3.89 (dt, J=10.7, 3.2 Hz, 1H), 2.89 (d, J=12.6 Hz), 2.29 (dd, J=13.3, 11.5 Hz, 1H), 2.05-1.94 (m, 8H), 1.69 (s, 6H), 1.61 (s, 3H), 1.59 (s, 3H), 1.57 (s, 3H), 1.53 (s, 3H);

$^{13}$C NMR (CDCl$_3$), δ (ppm): 145.0, 139.6, 138.0, 135.6, 135.0, 133.3, 131.4, 129.8, 129.2, 129.2, 128.7, 128.7, 128.2, 124.2, 124.0, 123.5, 123.4, 117.3, 63.6, 59.4, 39.7, 39.7, 39.5, 39.3, 37.3, 26.7, 26.6, 26.4, 26.3, 25.7, 17.7, 16.3, 16.3, 15.9, 15.9, 15.9.

Example 10

Hexaprenol

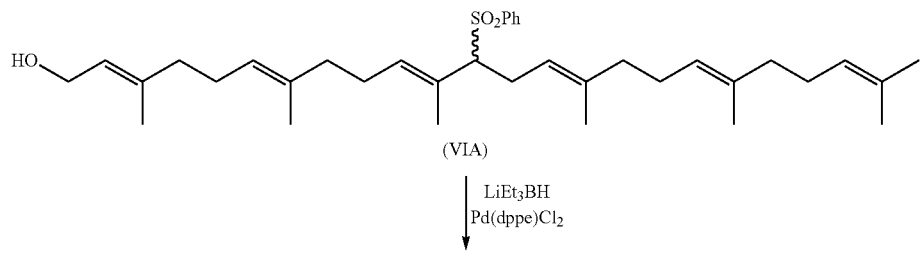

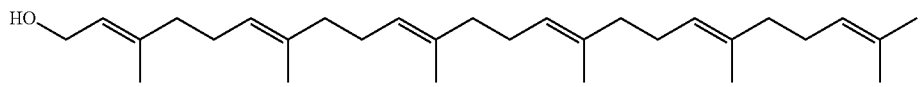

In a reaction vessel (2.5 L capacity) equipped with CaCl$_2$ tube, thermocouple, mechanic stirrer, nitrogen line adapter, immersed in a cooling bath (acetone/CO$_2$), the mixture of sulfone VIA (57.36 g) and THF (400 mL) was stirred under N$_2$ for 5 min, and then cooled to 0° C. A this temperature, Pd(dppe)Cl$_2$ catalyst (1.75 g) was added, followed by dropwise addition of 1 M LiEt$_3$BH (303 ml) within 40 min. Reaction progress was monitored by TLC. After 30 min. to the reaction mixture water (300 mL), MeOH (50 mL), 20% NH$_4$Cl aq (350 mL) and toluene (350 mL) were added. The resulting solution was transferred into the separatory funnel. Organic phase was separated and evaporated to dryness under vacuum. The residue was diluted with toluene (2×100 mL) and hexane (1×200 mL). Solvents were evaporated to dryness each time. Last portion of hexane (250 mL) was added producing the suspension, which was filtered through celite pad (20 g) in a Schott G3 funnel and was washed with hexane (250 mL). The filtrate was evaporated to dryness under reduced pressure using high vacuum in the end of the process (<1 mmHg). The oily product was obtained in 46.85 g yield.

The oil was purified by column chromatography 1 (silica gel), eluent:
hexane:ethyl acetate 20:1→hexane:ethyl acetate 9:1→hexane:ethyl acetate 4:10, hexaprenol yield 75.5%.

$^1$H NMR (CDCl$_3$), δ (ppm): 5.45-5.41 (m, 1H), 5.14-5.09 (m, 5H), 4.16 (d, J=7.0 Hz, 2H), 2.12-1.99 (m, 20H), 1.69 (s, 6H), 1.61 (s, 12H), 1.56 (s, 3H);

$^{13}$C NMR (CDCl$_3$), δ (ppm): 139.7, 135.3, 134.9, 134.9, 134.8, 131.2, 124.4, 124.2, 124.2, 124.2, 123.7, 123.4, 123.4, 39.7, 36.5, 26.7, 26.7, 26.6, 26.3, 25.6, 17.6, 16.2, 16.0×4;

ESI-MS: 449 (M$^+$Na$^+$).

Example 11

Hexaprenyl Bromide

In a reaction vessel (750 mL capacity), equipped with CaCl$_2$ tube, thermocouple, mechanic stirrer, nitrogen line adapter, immersed in a cooling bath (acetone/CO$_2$), hexaprenol (31.6 g) was dissolved in anhydrous THF (140 mL). The mixture was stirred under N$_2$ for 5 min. and cooled to 0° C. At this temperature, PBr$_3$ (3 mL) was added dropwise (10 min). After 10 min. starting material was entirely consumed (TLC). Stirring was continued at 0° C. for additional 20 min. 5% NaHCO$_3$ (170 mL) was added dropwise at 5-10° C. The mixture was diluted with ethyl acetate (130 mL) and brine (90 mL), vigorous stirring was continued for 5 min. Organic phase was separated and evaporated under reduced pressure. Toluene (50 mL) was added and solvent was evaporated to dryness again, using high vacuum in the end of evaporation (<1 mmHg). Bromide VIIA was obtained as an oil in 36.5 g (99%) yield.

$^1$H NMR (CDCl$_3$), δ (ppm): 1.47 (15H, 5× CH$_3$); 1.55 (3H, CH$_3$), 1.59 (3H, CH$_3$), 1.72- 2.04 (20H, 10× CH$_2$), 3.88 (2H, CH$_2$—Br), 4.98 (5H, 5× CH), 5.40 (1H, CH);

$^{13}$C NMR (CDCl$_3$), δ (ppm): 15.94 (CH$_3$); 15.99 (CH$_3$); 16.03 (CH$_3$); 17.65 (CH$_3$); 25.68 (CH$_3$); 26.07 (CH$_2$); 26.21 (CH$_2$); 26.59 (CH$_2$); 26.64 (CH$_2$); 26.74 (CH$_2$); 26.91 (CH$_2$); 29.58 (CH$_2$—Br); 39.21 (CH$_2$); 39.51 (CH$_2$); 39.70 (CH$_2$); 120.53 (CH); 123.25 (CH); 123.34 (CH); 124.14 (CH); 124.23 (CH); 124.38 (CH); 131.18 (C); 134.84 (C); 134.88 (C); 134.94 (C); 135.61 (C); 135.73 (C); 143.54 (C).

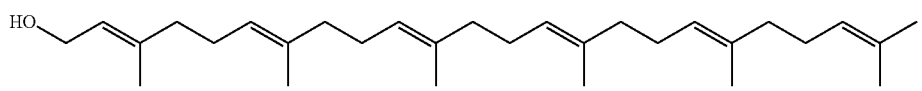

(VI)

PBr$_3$

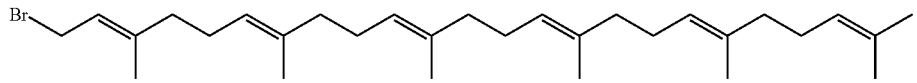

(VIIA)

Example 12

12-Phenylsulfonyl Hexaprenyl Bromide

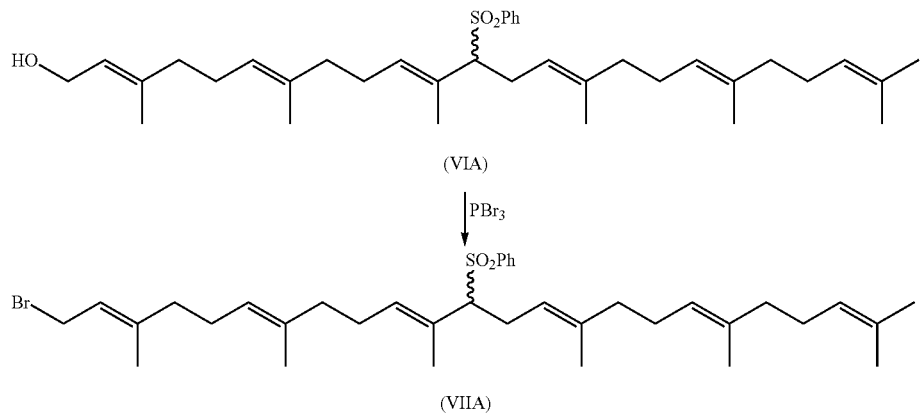

In a reaction vessel (three-neck flask 25 mL) equipped with CaCl$_2$ tube, thermocouple, magnetic stirrer, nitrogen line adapter, immersed in a cooling bath (acetone/CO$_2$), the compound VIA (3 g) was stirred under N$_2$ for 5 min. in anhydrous THF (14 mL). The mixture was cooled to 0° C. and PBr$_3$ (0.215 mL) was added dropwise for 10 min. while maintaining temp. 2-3° C. After PBr$_3$ addition, the mixture was stirred for further 20 min. at 0° C. and 5% NaHCO3 (17 mL) was carefully added, while maintaining temp. 5-10° C. To the resulting mixture ethyl acetate (14 mL) and brine (9 mL) were quickly added, stirred vigorously and transferred into separatory funnel. Organic phase was separated and transferred into a round bottom flask to remove solvent to dryness under reduced pressure. Toluene (6 mL) was added and drying procedure was repeated. The compound VIIA was obtained as an oil, in 3.35 g yield (calc. yield 3.33 g).

$^1$H NMR (CDCl$_3$), δ (ppm): 1.52 (3H, CH$_3$); 1.56 (3H, CH$_3$), 1.59 (6H, 2× CH$_3$), 1.65 (3H, CH$_3$), 1.67 (3H, CH$_3$), 1.72 (3H, CH$_3$), 1.69-2.12 (16H, 8× CH$_2$), 2.48-2.90 (2H, —CH(SO$_2$Ph)-CH$_2$—), 3.47 (1H, —CH(SO$_2$Ph)-CH$_2$—), 4.02 (2H, CH$_2$—Br), 4.88 (1H, CH), 5.05 (4H, 4× CH), 5.50 (1H, CH), 7.55 (3H, 3× CH$_{ar}$), 7.82 (2H, 2× CH$_{ar}$);

$^{13}$C NMR (CDCl$_3$), δ (ppm): 13.71 (CH$_3$); 15.89 (CH$_3$); 15.92 (CH$_3$); 16.24 (CH$_3$); 17.63 (CH$_3$); 23.97 (—CH(SO$_2$Ph)-CH$_2$—); 25.64 (CH$_3$); 25.94 (CH$_2$); 26.44 (CH$_2$); 26.69 (CH$_2$); 29.53 (CH$_2$—Br); 38.50 (CH$_2$); 39.34 (CH$_2$); 39.59 (CH$_2$); 39.65 (CH$_2$); 73.99 (CH—SO$_2$Ph); 118.67 (CH); 120.58 (CH); 123.62 (CH); 123.76 (CH); 124.22 (CH); 126.48 (C); 128.62 (CH); 128.83 (CH); 131.23 (C); 133.22 (CH); 134.88 (C); 135.10 (C); 135.64 (CH); 138.04 (C); 138.31 (C); 143.32 (C).

Example 13

Diphenylsulfonyl Heptaprenyl Dimethoxymenadiol

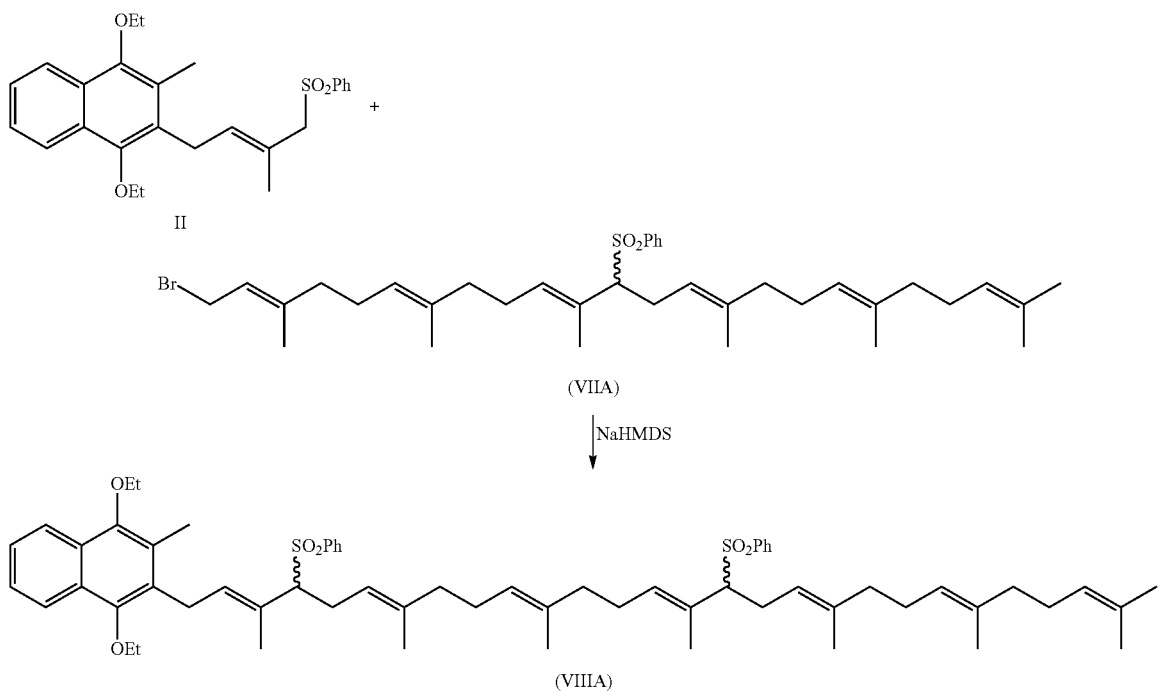

In a reaction vessel equipped with CaCl$_2$ tube, thermocouple, magnetic stirrer, nitrogen line adapter, immersed in a cooling bath (acetone/CO$_2$), phenylsulfone II (2.27 g) was placed in the mixture of THF (20 mL) and DMF (4 mL). The solution was stirred under N$_2$, until the solution was uniform, then the compound VIIA (3.33 g) in THF (10 mL) was added. 1 M NaHMDS in THF (5.5 mL) was added dropwise at −20° C. in 10 min. The resulting solution was stirred at

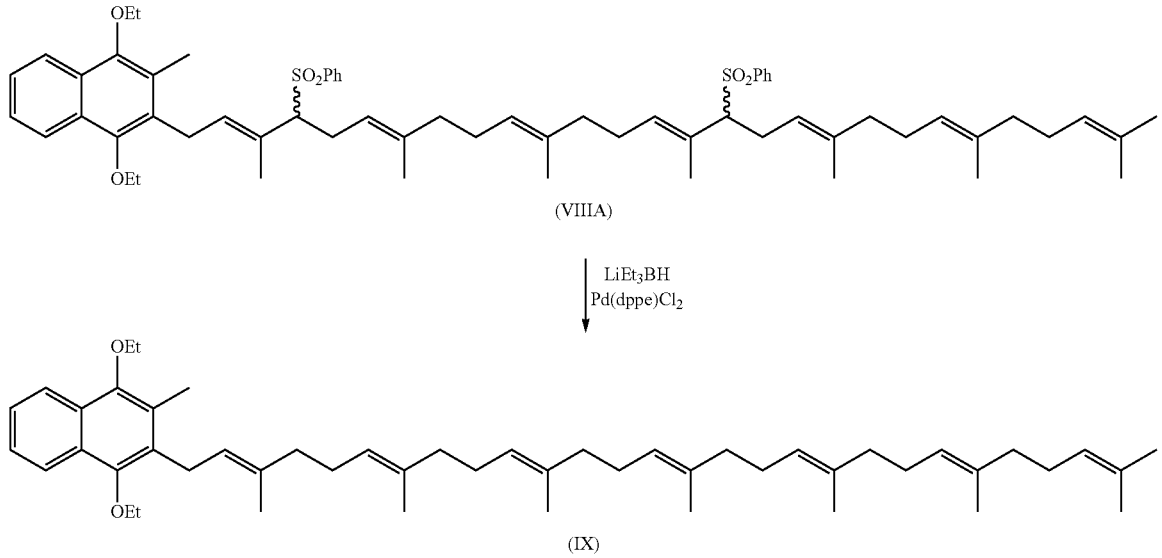

−20° C. for 20 min, then the mixture was warm up to 0° C., then subsequently 20% NH$_4$Cl (30 mL) and ethyl acetate (15 mL) were added. The mixture was transferred into a separatory funnel to separate phases. Organic layer was condensed to dryness in a round bottom flask under vacuum. To the residue toluene (15 mL) was added and the solvent was removed to dryness again. Another portion of toluene (8 mL) was added, the solution was filtered through a Schott G3 funnel, washed with toluene (2 mL), the filtrate was condensed to dryness under reduced pressure, yielding the crude oily product (5.68 g).

The product was purified by column chromatography (silica gel, eluents; hexane:ethyl acetate 9:1, 4:1, 2:1), the compound VIIIA was obtained in 4.91 g (96.0%) yield.

$^1$H NMR (CDCl$_3$), δ (ppm): 1.47 (3H, CH$_3$); 1.48 (6H, 2× CH$_3$), 1.56 (3H, CH$_3$), 1.58 (9H, 3× CH$_3$), 1.64 (3H, CH$_3$), 1.66 (3H, CH$_3$), 1.90 (3H, CH$_3$), 2.14 (3H, CH$_3$), 1.68-2.08 (16H, 8× CH$_2$), 2.44-2.92 (4H, 2×—CH(SO$_2$Ph)-CH$_2$—), 3.30-3.56 (4H, CH$_2$+2×—CH(SO$_2$Ph)-CH$_2$—), 3.83 (2H, —CH$_2$—O), 3.92 (2H, —CH$_2$—O), 4.80-5.14 (7H, 7× CH), 7.20-7.64 (8H, 8× CH$_{ar}$), 7.66-7.84 (4H, 4× CH$_{ar}$), 7.90-8.08 (2H, 2× CH$_{ar}$);

$^{13}$C NMR (CDCl$_3$), δ (ppm): 12.56 (CH$_3$); 13.72 (CH$_3$); 13.85 (CH$_3$); 14.11 (CH$_3$); 15.72 (CH$_3$); 15.78 (CH$_3$); 15.88 (CH$_3$); 16.20 (CH$_3$); 16.22 (CH$_3$); 17.60 (CH$_3$); 23.82 (—CH(SO$_2$Ph)-CH$_2$—); 23.99 (—CH(SO$_2$Ph)-CH$_2$—); 25.62 (CH$_3$); 26.41 (CH$_2$); 26.51 (CH$_2$); 26.60 (CH$_2$); 26.66 (CH$_2$); 26.78 (CH$_2$); 38.53 (CH$_2$); 39.56 (CH$_2$); 39.59 (CH$_2$); 39.63 (CH$_2$); 69.44 (—CH$_2$—O); 70.15 (—CH$_2$—O); 73.74 (CH—SO$_2$Ph); 73.93 (CH—SO$_2$Ph); 118.55 (CH); 118.65 (CH); 122.11 (CH); 122.21 (CH); 123.73 (CH); 124.00 (CH); 124.19 (CH); 125.17 (CH); 125.41 (CH); 126.34 (C); 126.47 (C); 127.20 (C); 127.33 (C); 127.82 (C); 128.54 (C); 128.57 (CH); 128.60 (C); 128.79 (CH); 128.87 (C); 131.19 (C); 133.12 (CH); 133.19 (CH); 134.30 (CH); 134.50 (C); 135.07 (C); 135.56 (CH); 137.69 (C); 138.03 (C); 138.28 (C); 138.44 (C); 148.69 (C); 149.04 (C).

Example 14

Heptaprenyl Diethoxymenadiol

In a reaction vessel equipped with CaCl$_2$ tube, thermocouple, magnetic stirrer, nitrogen line adapter, immersed in a cooling bath (acetone/CO$_2$), the compound VIIIA (4.7 g) and Pd (dppe)Cl$_2$ catalyst (125 mg) in THF (21 mL) were placed. The mixture was stirred under N$_2$ for 5 min., it was cooled to 0° C., then 1 M LiEt$_3$BH (21 mL) was added dropwise in 5 min. The resulting mixture was stirred at 0° C. for 4.5 h. To the reaction mixture water (20 mL), EtOH (2 mL), brine (20 mL) and toluene (20 mL) were carefully added. The resulting mixture was transferred into a separatory funnel, organic phase was washed with 20% brine (2×10 mL), then evaporated to dryness under reduced pressure. 10 mL of toluene was added and evaporated to dryness. Further 10 mL of toluene were added and celite (0.5 g), the filtrate was evaporated to dryness. The residue was diluted with hexane (2×10 mL), the solvent was evaporated to dryness, another portion of hexane was added (20 mL) and the resulting suspension was filtered through celite (2 g) bed in a Schott G3 funnel, which was washed with hexane (20 mL). The collected filtrate was evaporated to dryness. The product was obtained as colorless oil (3.06 g).

The crude product was purified by column chromatography, with gradient elution in hexane:ethyl acetate 50:1-20:1. The product was obtained in 2.68 g (80%) yield. It was used directly in the next step.

$^1$H NMR (CDCl$_3$, 50 MHz), δ (ppm): 1.53 (6H, 2× CH$_3$); 1.57 (6H, 2× CH$_3$), 1.59 (4H, 4× CH$_3$), 1.68 (3H, CH$_3$), 1.82 (3H, CH$_3$), 1.88-2.18 (24H, 12× CH$_2$), 2.36 (3H, CH$_3$), 3.97 (4H, 2×—CH$_2$—O), 5.00-5.28 (7H, 7× CH), 7.34-7.50 (2H, 2× CH$_{ar}$), 7.96- 8.12 (2H, 2× CH$_{ar}$);

$^{13}$C NMR (CDCl$_3$, 200 MHz), δ (ppm): 12.68 (CH$_3$); 15.80 (CH$_3$); 15.89 (CH$_3$); 16.40 (CH$_3$); 17.67 (CH$_3$); 25.80 (CH$_3$); 26.48 (CH$_2$); 26.56 (CH$_2$); 26.66 (CH$_2$); 26.75 (CH$_2$); 39.71 (CH$_2$); 69.48 (—CH$_2$—O); 70.39 (—CH$_2$—

O); 122.17 (CH); 122.31 (CH); 122.99 (CH); 124.03 (CH); 124.16 (CH); 124.25 (CH); 124.40 (CH); 125.04 (CH); 125.17 (CH); 127.03 (C); 127.52 (C); 127.75 (C); 130.91 (C); 131.22 (CH); 134.89 (C), 134.93 (C); 135.07 (C); 135.58 (C); 148.70 (C); 149.08 (C).

Example 15

Vitamin MK-7

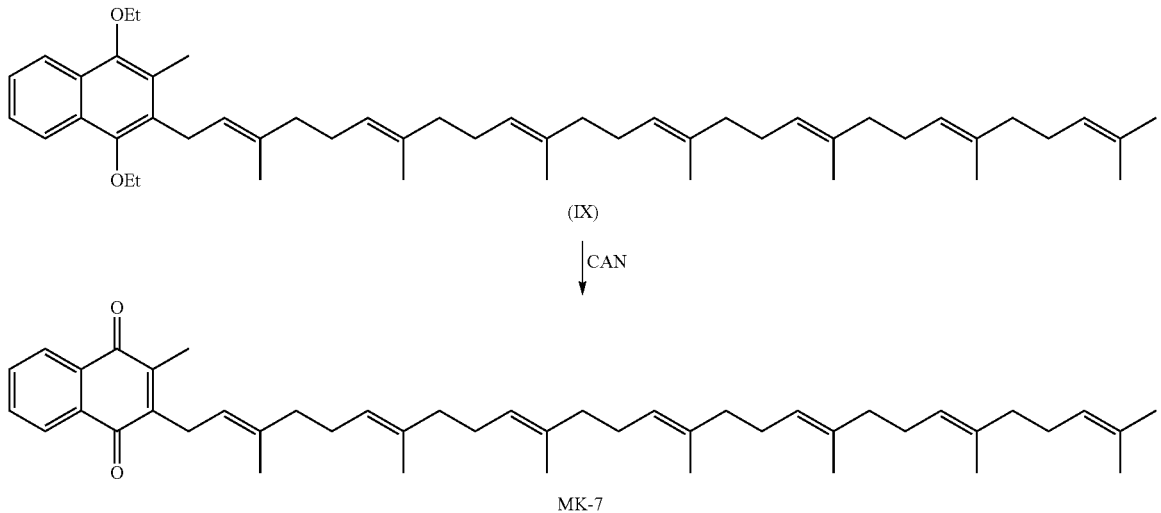

In a reaction vessel equipped with thermocouple and magnetic stirrer, obtained in the Example 14 the oily product (2.68 g, 2.8 mmol), was placed in the mixture of $CH_3CN$:$CH_2Cl_2$ (30 mL, 1:1). When the solution became homogenous, it was cooled down to 5° C. In a separate vessel the solution of cerium ammonium nitrate $Ce(NH_4)_2(NO_3)_6$ (CAN) (5.2 g, 0.353 mol) was dissolved in acetonitrile-water (30 ml, 9:1) mixture. CAN (29.3 g, 5.2 g CAN) solution was added dropwise to the reaction mixture at 4-5° C. After 20 min. stirring at 4-5° C., water (41 mL) was added dropwise. The two-phase mixture was transferred into a separatory funnel, organic layer was separated, washed with brine-water mixture (16 mL, 1:1) and saturated brine solution (16 mL). Organic phase was evaporated to dryness under reduced pressure. The crude product was obtained as an oil in 2.45 g yield.

The crude product was subjected to chromatography on silica gel, using gradient eluent: hexane:ethyl acetate 4:1→1:1.2 g of crude vitamin MK-7 was obtained, that was crystallized in ethyl acetate/ethanol.

Crystallization 1

To the solution of the crude product (2 g) dissolved in ethyl acetate (4 mL) at RT, anhydrous EtOH (20 mL) was added. The resulting mixture was stirred at RT for 24 h. The solid was filtered off and washed with cold (0° C.) EtOH (10 mL). The crystalline product of 98.85% purity (HPLC) was obtained in 1.22 g (49.6%) yield.

M.p. 54.68° C. (DSC);

$^1$H NMR (CDCl$_3$, 50 MHz), δ (ppm): 1.56 (6H, s), 1.59 (12H, s), (1.67 (3H, s), 1.80 (3H, s), 1.84-2.26 (24H, m), 2.18 (3H, s), 3.36 (2H, d (7.0 Hz)), 4.86-5.28 (7H, m), 7.56-7.78 (2H, m), 7.96-8.16 (2H, m);

$^{13}$C NMR (CDCl$_3$, 200 MHz), δ (ppm): 12.58 (CH$_3$), 15.95 (CH$_3$), 16.35 (CH$_3$), 17.61 (CH$_3$), 25.63 (CH$_3$), 25.93 (CH$_2$), 26.43 (CH$_2$), 26.63 (CH$_2$), 26.70 (CH$_2$), 39.66 (CH$_2$), 119.04 (CH), 123.79 (CH), 124.10 (CH), 124.22 (CH), 124.37 (CH), 126.11 (CH), 126.22 (CH), 131.11 (C), 132.07 (C), 132.11 (C), 133.16 (C), 133.21 (C), 134.80 (C), 135.12 (C), 137.44 (C), 143.24 (C), 146.04 (C), 184.36 (C=O), 185.28 (C=O).

Example 16

Phenylsulfonyl Heptaprenyl Diethoxymenadiol

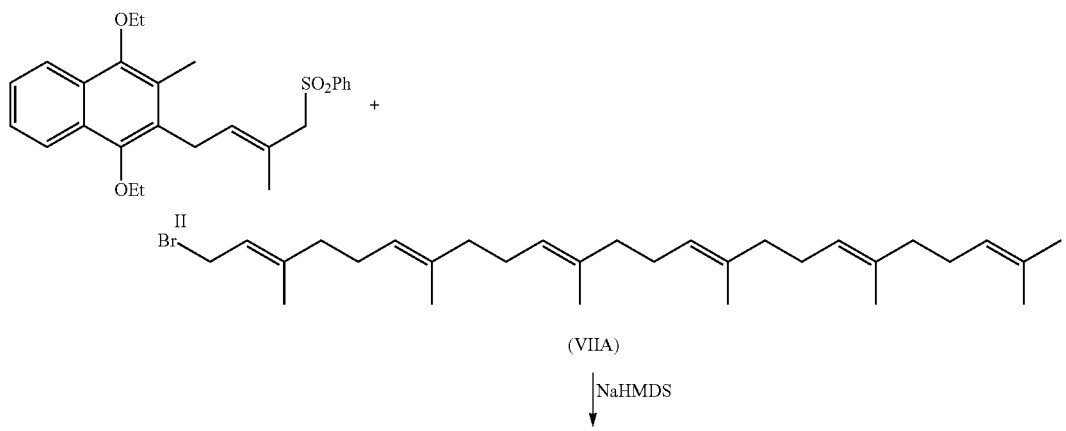

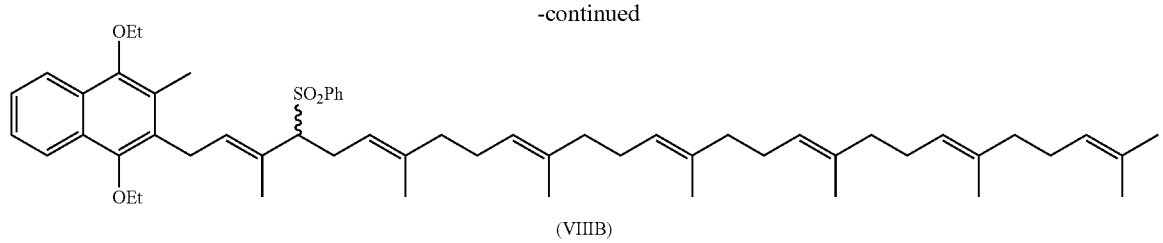

(VIIIB)

In a reaction vessel equipped with CaCl$_2$ tube, thermocouple, magnetic stirrer and nitrogen line adapter, immersed in a cooling bath (acetone/dry ice), sulfone II (60 g, 136.8 mmol) in the mixture of DMF (90 mL) and THF (200 mL) was placed. The solution was stirred under N$_2$ until it became homogenous, then hexaprenyl bromide VIIA (69.02 g 140.9 mmol) in THF (200 mL) was added. The resulting mixture was cooled down to −20° C., then 1M NaHMDS in THF (147 mL) was added in 40 min. The solution became yellow. After 10 min. the starting material was entirely consumed (TLC). The stirring was continued at −20° C. for 20 min., the solution was warmed to 0° C. and 20% NH$_4$Cl (800 mL) and ethyl acetate (400 mL) were added. Organic phase was separated and condensed to dryness under reduced pressure. Toluene (400 mL) was added and the solvent was evaporated to dryness under vacuum again. The residue was diluted with toluene (200 mL) and filtrated through a Schott G3 funnel, washed with toluene (80 mL). The filtrate was condensed to dryness under reduced pressure, using high vacuum in the end of the process (<1 mmHg). 119.09 g of oily product was obtained. The crude product was purified by column chromatography (silica gel, hexane:ethyl acetate 20:1 and hexane:ethyl acetate 9:1), yielding 100.62 g (86.8%) of sulfone (VIIIB).

$^1$H NMR (CDCl$_3$), δ (ppm): 1.48 (6H, 2× CH$_3$), 1.55 (3H, CH$_3$), 1.58 (15H, 5× CH$_3$), 1.68 (3H, CH$_3$), 1.90 (3H, CH$_3$), 1.84-2.12 (20H, 10× CH$_2$), 2.14 (3H, CH$_3$), 2.50-2.92 (2H, —CH(SO$_2$Ph)-CH$_2$—), 3.30-3.58 (3H, CH$_2$+ —CH(SO$_2$Ph)-CH$_2$—), 3.82 (2H, —CH$_2$—O), 3.92 (2H, —CH$_2$—O), 4.96-5.18 (6H, 6× CH), 4.88 (1H, CH), 7.26-7.50 (5H, 5× CH$_{ar}$), 7.68-7.78 (2H, 2× CH$_{ar}$), 7.90-8.08 (2H, 2× CH$_{ar}$);

$^{13}$C NMR (CDCl$_3$), δ (ppm): 12.60 (CH$_3$); 13.91 (CH$_3$); 15.75 (CH$_3$); 15.82 (CH$_3$); 15.96 (CH$_3$); 16.25 (CH$_3$); 17.64 (CH$_3$); 23.85 (—CH(SO$_2$Ph)-CH$_2$—); 25.65 (CH$_3$); 26.28 (CH$_2$); 26.52 (CH$_2$); 26.65 (CH$_2$); 26.90 (CH$_2$); 39.24 (CH$_2$); 39.29 (CH$_2$); 39.68 (CH$_2$); 69.48 (—CH$_2$—O); 70.21 (—CH$_2$—O); 73.80 (CH—SO$_2$Ph); 118.49 (CH); 122.14 (CH); 122.25 (CH); 123.14 (CH); 123.19 (CH); 123.67 (CH); 124.10 (CH); 124.20 (CH); 124.35 (CH); 125.19 (CH); 125.42 (CH); 126.41 (C); 127.23 (C); 127.38 (C); 127.87 (C); 128.58 (CH); 128.95 (C); 131.18 (C); 133.12 (CH); 134.38 (CH); 134.88 (C); 134.95 (C); 135.26 (C), 137.79 (C); 138.60 (C); 148.73 (C); 149.09 (C).

Example 17

Heptaprenyl Diethoxymenadiol

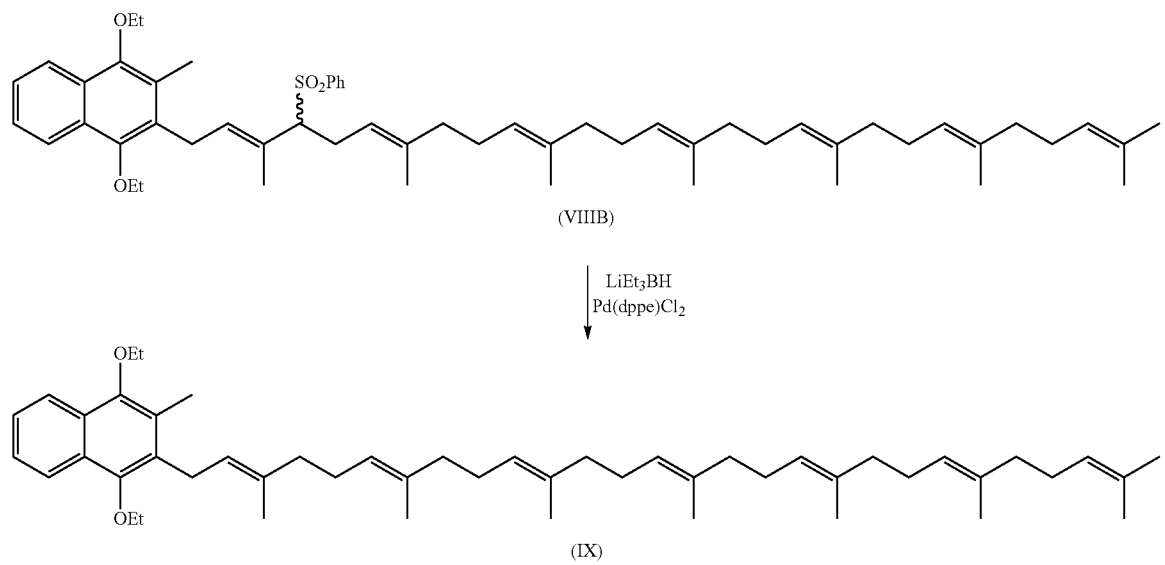

In a reaction vessel equipped with CaCl$_2$ tube, thermocouple, magnetic stirrer and nitrogen line adapter, immersed in a cooling bath (acetone/dry ice), the solution of sulfone (VIIIB) (100.5 g, 118.6 mmol) and Pd(dppe)Cl$_2$ (2.07 g, 3.6 mmol) catalyst in THF (400 mL) were placed. The mixture was stirred under N₂ for 5 min., then it was cooled down to 0° C. and 1M LiEt₃BH in THF (260 mL) was added in 5 min. Stirring was continued at 0° C. for 5 h. To the solution water (400 mL) was added, followed by EtOH (40 mL), brine (400 mL) and toluene (400 mL) addition. The mixture was transferred into a separatory funnel, organic phase was separated and washed with 20% NH₄Cl aq. (200 mL). The solvents were evaporated to dryness, to the residue hexane (2×200 mL) was added, then it was removed do dryness. Another portion of heptane was added (400 mL) and the suspension was filtered through a Schott G3 funnel, washed with hexane (400 mL). The filtrate was condensed to dryness under high vacuum in the end of the process. The crude product was obtained in 84.2 g yield (calc. yield 83.97 g).

The crude product was purified by column chromatography, eluting with hexane:ethyl acetate 25:1 and 20:1. The pure product was obtained in 81.25 g (96.8%) yield.

¹H NMR (CDCl₃), δ (ppm): 1.53 (6H, 2× CH₃); 1.57 (6H, 2× CH₃), 1.59 (4H, 4× CH₃), 1.68 (3H, CH₃), 1.82 (3H, CH₃), 1.88-2.18 (24H, 12× CH₂), 2.36 (3H, CH₃), 3.97 (4H, 2×—CH₂—O), 5.00-5.28 (7H, 7× CH), 7.34-7.50 (2H, 2× CH$_{ar}$), 7.96-8.12 (2H, 2× CH$_{ar}$);

¹³C NMR (CDCl₃), δ (ppm): 12.68 (CH₃); 15.80 (CH₃); 15.89 (CH₃); 16.40 (CH₃); 17.67 (CH₃); 25.80 (CH₃); 26.48 (CH₂); 26.56 (CH₂); 26.66 (CH₂); 26.75 (CH₂); 39.71 (CH₂); 69.48 (—CH₂—O); 70.39 (—CH₂—O); 122.17 (CH); 122.31 (CH); 122.99 (CH); 124.03 (CH); 124.16 (CH); 124.25 (CH); 124.40 (CH); 125.04 (CH); 125.17 (CH); 127.03 (C); 127.52 (C); 127.75 (C); 130.91 (C); 131.22 (CH); 134.89 (C), 134.93 (C); 135.07 (C); 135.58 (C); 148.70 (C); 149.08 (C).

Example 18

Vitamin MK-7

In a reaction vessel (three-neck flask 25 mL), equipped with thermocouple and magnetic stirrer, the oily compound (IX) obtained in Example 17 (1.89 g, 2.8 mmol) in the mixture of CH₃CN:CH₂CL₂ (21 mL, (1:1)) was placed. At 0° C. CAN (3.84 g, 7 mmol) in the mixture of CH₃CN:H₂O (21 mL, 6:1) was added dropwise. After 15 min. to the reaction solution the mixture of water and ice (200 mL) was added and the product was extracted with CH₂CL₂ (3×100 mL). Combined organic extracts were washed with water, dried over anhydrous Na₂SO₄ and condensed under vacuum.

The crude product was pre-purified by "dry flesh" column chromatography (hexane:dichloromethane, 5:1), yielding 1.29 mg (1.99 mmol, 72%) of pure fraction of oily product of 99.4% purity (HPLC).

Chromatographically purified oily product was crystallized in ethyl acetate (0.24 mL) with addition of anhydrous ethanol (0.8 mL) upon stirring for 2 h at 10° C. Vitamin MK-7 of 99.9% purity (HPLC) was obtained.

M.p. 54.68° C. (DSC);

¹H NMR (CDCl₃, 50 MHz), δ (ppm): 1.56 (6H, s), 1.59 (12H, s), (1.67 (3H, s), 1.80 (3H, s), 1.84-2.26 (24H, m), 2.18 (3H, s), 3.36 (2H, d (7.0 Hz)), 4.86-5.28 (7H, m), 7.56-7.78 (2H, m), 7.96-8.16 (2H, m);

¹³C NMR (CDCl₃, 200 MHz), δ (ppm): 12.58 (CH₃), 15.95 (CH₃), 16.35 (CH₃), 17.61 (CH₃), 25.63 (CH₃), 25.93 (CH₂), 26.43 (CH₂), 26.63 (CH₂), 26.70 (CH₂), 39.66 (CH₂), 119.04 (CH), 123.79 (CH), 124.10 (CH), 124.22 (CH), 124.37 (CH), 126.11 (CH), 126.22 (CH), 131.11 (C), 132.07 (C), 132.11 (C), 133.16 (C), 133.21 (C), 134.80 (C), 135.12 (C), 137.44 (C), 143.24 (C), 146.04 (C), 184.36 (C=O), 185.28 (C=O).

ESI-MS: 672 (M+Na⁺).

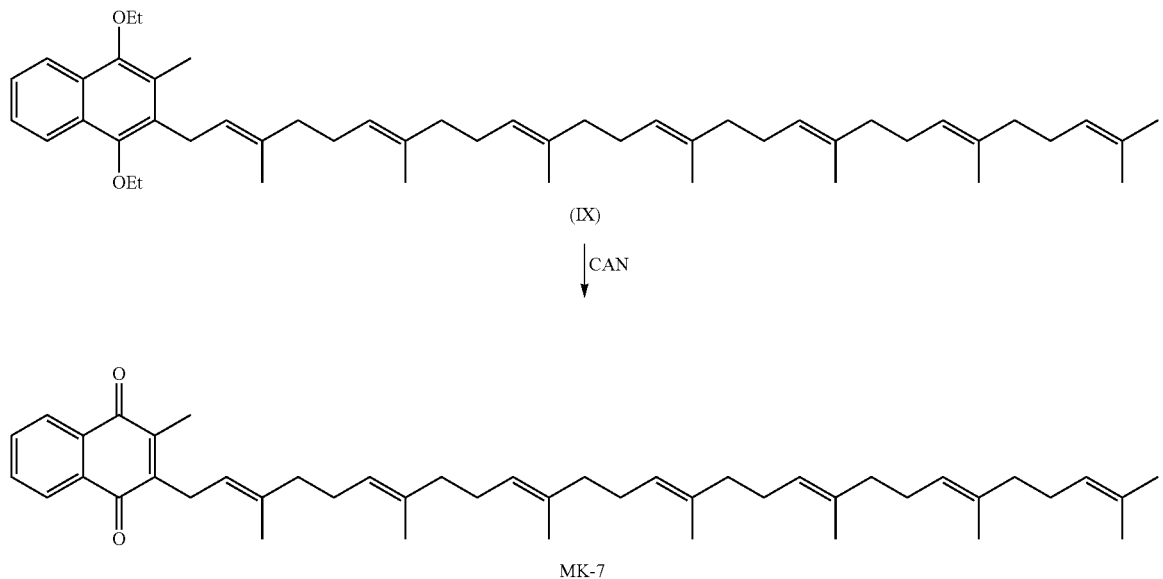

Example 19

Phenylsulfonyl Heptaprenyl Dimethoxymenadiol

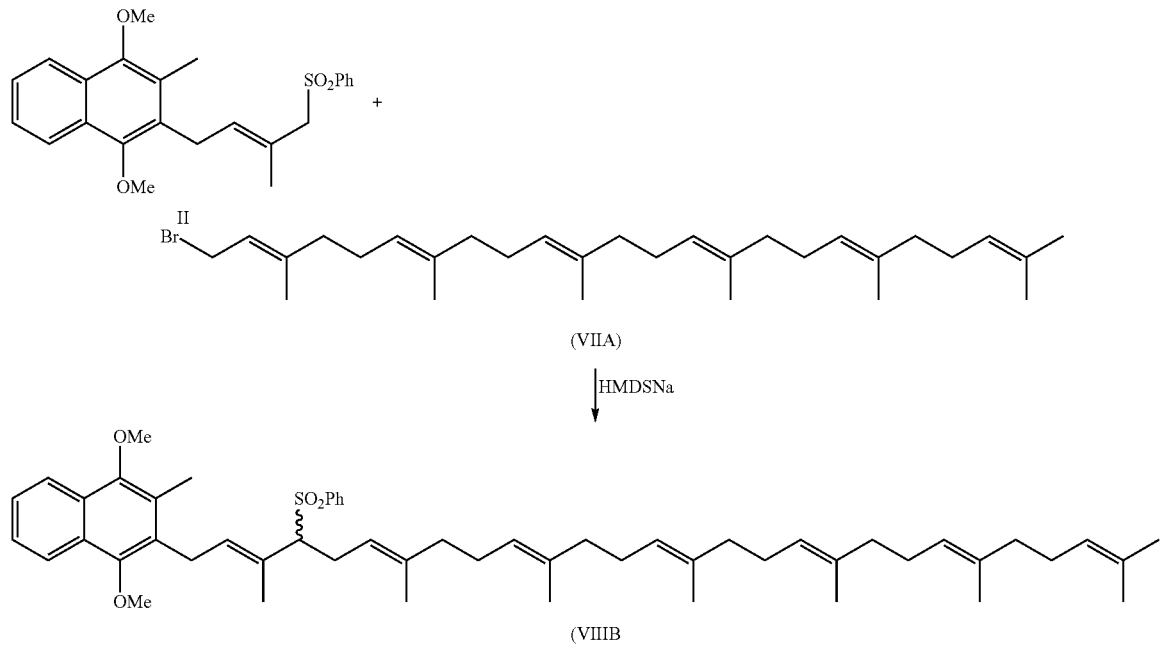

In a reaction vessel equipped with CaCl$_2$ tube, thermocouple, magnetic stirrer, nitrogen line adapter, immersed in a cooling bath (acetone/CO$_2$), phenylsulfone (II) (13.76 g) in the mixture of DMF (20 mL) and THF (150 mL) was placed. The solution was stirred under N$_2$, when the solution became homogenous, MK-1 (18 g) in THF (50 mL) was added. To the resulting mixture, 1M HMDSNa (40 mL) in THF, at −20° C. in 40 min. was added (the solution became yellow). After 10 min. reaction was completed (TLC). Stirring was continued at −20° C. for 20 min. When the mixture reached 0° C., 20% NH$_4$Cl (200 mL) and ethyl acetate (100 mL) were added. Organic phase was separated and condensed to dryness under reduced pressure. The residue was diluted with toluene (100 mL) and the solvent was removed under vacuum. After addition of another portion of toluene (50 mL), the solution was filtered through a Schott G3 funnel, washed with toluene (20 mL), the filtrate was condensed to dryness, using high vacuum in the end of drying (<1 mmHg). 30.73 g of the oily product was obtained. It was chromatographed (silica gel, hexane:ethyl acetate—9:1), to afford sulfone in 26.03 g (95.0%) yield.

$^1$H NMR (CDCl$_3$), δ (ppm): 8.06-7.99 (m, 2H), 7.75 (d, J=7 Hz), 7.49-7.31 (m, 5H), 5.14-5.03 (m, 6H), 4.89 (t, J=6.9 Hz), 3.84 (s, 3H), 3.74 (s, 3H), 3.52-3.38 (m, 3H), 2.85-2.80 (m. 1H), 2.70-2.62 (m, 1H), 2.17 (s, 3H), 2.07-1.96 (m, 20H), 1.91 (s, 3H), 1.69 (s, 3H), 1.61 (s, 9H), 1.60 (s, 3H), 1.59 (s, 3H), 1.57 (s, 3H);

$^{13}$C NMR (CDCl$_3$), δ (ppm): 150.1, 149.8, 138.7, 137.9, 135.3, 135.0, 134.9, 134.3, 133.1, 131.2, 129.0, 128.6×4, 127.6, 127.4, 127.2, 126.3, 125.7, 125.4, 124.2, 124.1, 123.7, 122.2, 122.1, 122.1, 118.5, 73.9, 62.0, 61.3, 39.7, 26.8, 26.7, 26.7, 26.7, 26.5, 26.5, 25.7, 23.9, 17.7, 16.3, 16.0, 13.9, 12.4, 12.4;

ESI-MS: 824 (M+Na+); EI-MS: 819.

Example 20

Heptaprenyl Dimethoxymenadiol

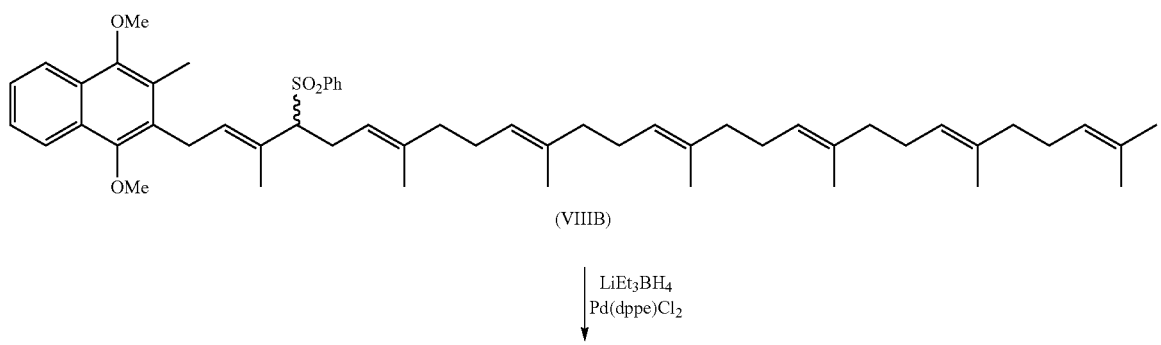

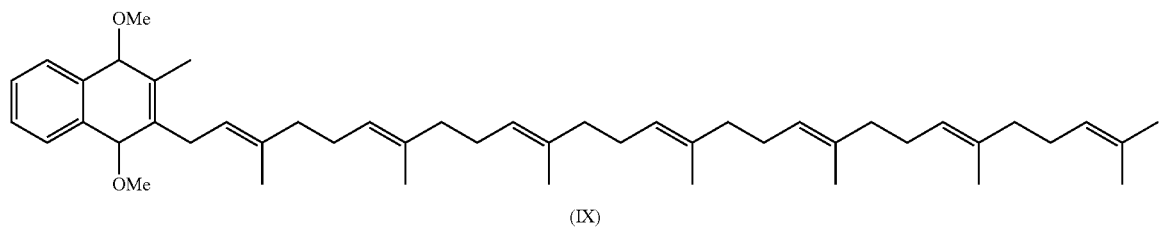

(IX)

In a reaction vessel equipped with CaCl$_2$ tube, thermocouple, magnetic stirrer, nitrogen line adapter, immersed in a cooling bath (acetone/CO$_2$), sulfone (VIIIB) (24.7 g, 30 mmol) in THF (100 mL) was placed. The solution was stirred under N$_2$, at 0° C. for 5 min., then Pd(dppe)Cl$_2$ catalyst (690 mg, 1.2 mmol) was added, followed by addition of 1M LiEt$_3$BH (66 mL) over a period of 5 min. Stirring was continued at 0° C. for 5 min. Water (100 mL), MeOH (10 mL), brine (100 mL) and toluene (100 mL) were added in succession. The mixture was transferred into a separatory funnel, organic phase was separated, filtered through celite (1 g) pad in a Schott G3 funnel. The filtrate was condensed to dryness under reduced pressure. The residue was diluted with hexane (100 mL) and condensed to dryness, using high vacuum in the end of drying. The product was obtained as colorless oil in 20.7 g (calc. yield 20.45 g) yield.

The obtained product was used directly in the next step of synthesis.

Example 21

Vitamin MK-7

In a reaction vessel (three-neck flask 25 mL), equipped with thermocouple, and magnetic stirrer, oil (IX) (1.89 g, 2.8 mmol) in the mixture of CH$_3$CN:CH$_2$CL$_2$ (21 mL, (1:1)) was placed. CAN (3.84 g, 7 mmol) in the mixture of CH$_3$CN:H$_2$O (21 ml, 6:1) at 0° was added dropwise. After 15 min., the reaction was quenched with water and ice (200 ml). The product was extracted with CH$_2$CL$_2$ (3×100 mL). Combined organic extracts were washed with water, dried over anhydrous Na$_2$SO$_4$ and condensed to dryness under reduced pressure.

The obtained product was pre-purified by "dry flesh" column chromatography (hexane:dichloromethane, 5:1), yielding 1.29 mg (1.99 mmol, 72%) of vitamin MK-7 of 99.4% purity (HPLC).

The chromatographically purified oily product was crystallized in ethyl acetate (0.24 mL) and anhydrous ethanol (0.8 mL), upon stirring at 10° C. for 2 h. Crystalline vitamin MK-7 of 99.9% purity (HPLC) was obtained.

The NMR spectra were identical to those disclosed in Example 18 and confirmed the molecular structure of vitamin MK-7.

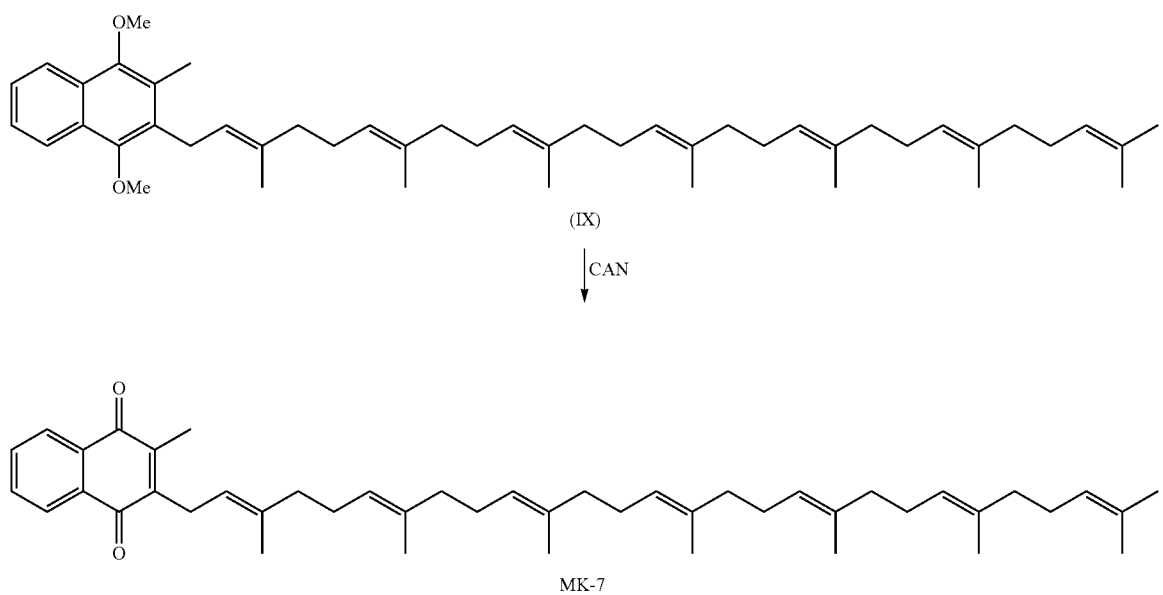

The invention claimed is:
1. A process for the preparation of MK-7 type of vitamin $K_2$, represented by formula (I)

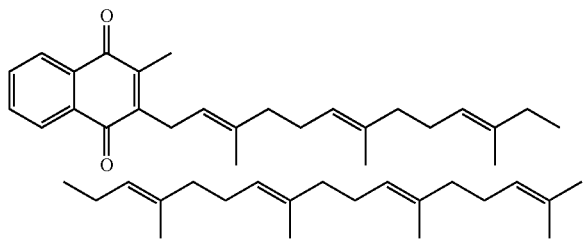

(I)

comprising the steps of
(a) reacting an α-sulfonyl carbanion generated in situ from the phenylsulfone of monoprenylmenadiol derivative of formula (II)

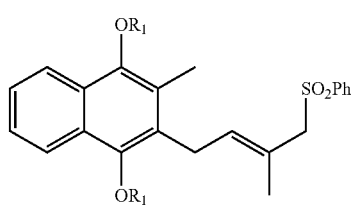

(II)

wherein $R_1$ represents $C_2$-alkyl, and wherein said phenylsulfone of monoprenylmenadiol derivative of formula (II) is in a crystalline form;
in the presence of a strong organometallic base,
with a hexaprenyl halide of formula (VII)

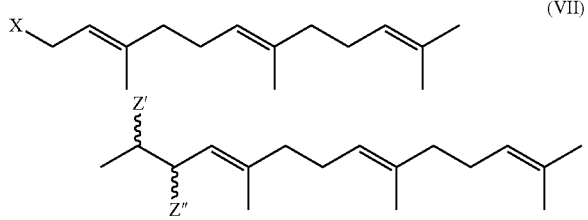

(VII)

wherein
X represents halogen,
one of Z' and Z" is H and the other is phenylsulfonyl —SO$_2$Ph group, as an alkylating agent;
to yield the phenylsulfonyl derivative of menadiol of the formula (VIII)

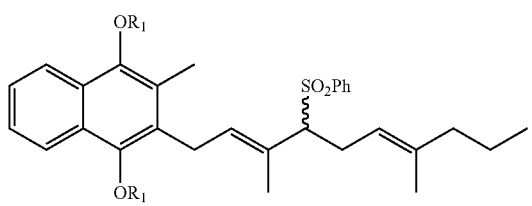

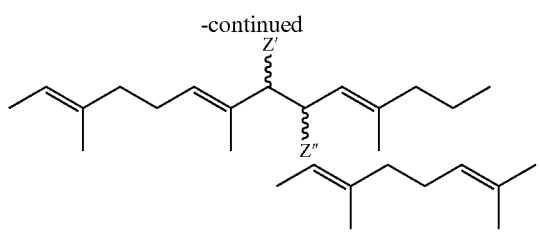

wherein $R_1$, Z' and Z" have the meaning defined above,
(b) removing the phenylsulfonyl groups from the menadiol derivative of formula (VIII) by the reductive elimination, to yield the menadiol derivative of formula (IX)

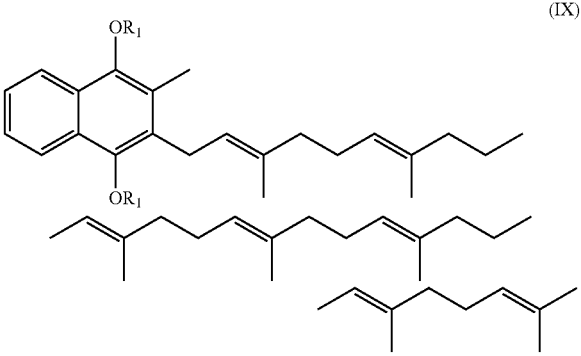

(IX)

wherein $R_1$ has the meaning defined above;
(c) subjecting the menadiol derivative of formula (IX) to an oxidative deetherification, to yield the crude menadione compound of formula (I), and

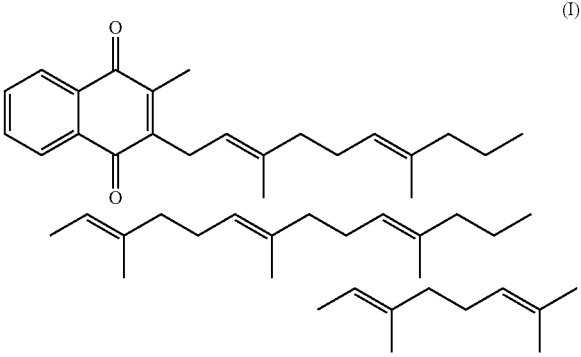

(I)

(d) optionally, purifying the crude menadione compound of formula (I) to yield pure MK-7.
2. The process according to claim 1, wherein the α-sulfonyl carbanion is generated by means of an alkali metal hexamethyldisilazyde, in a polar aprotic solvent.
3. The process according to claim 1, wherein the reductive elimination is accomplished by means of an alkali metal borohydride in the presence of an alkali metal (II) dihalide complex with bidentate ligands of phenylphosphine type of the general formula $[M\{Ph_2P(CH_2)_nPPh_2X_2\}]$, wherein n=2-5, X=Cl or Br, and M=Co, Ni or Pd, as catalysts.
4. The process according to claim 1, wherein the reductive elimination is accomplished by means of lithium triethylborohydride in the presence of Pd(dppe)Cl$_2$ complex, wherein dppe represents 1,2-bis(diphenylphosphino)ethane, or Pd(dppp)Cl$_2$, and wherein dppp represents 1,3-bis(diphenylphosphino)propane.
5. The process according to claim 1, wherein the oxidative deetherification is accomplished with the use of cerium ammonium nitrate.

6. The process according to claim 1, wherein the hexaprenyl halide of formula (VII)

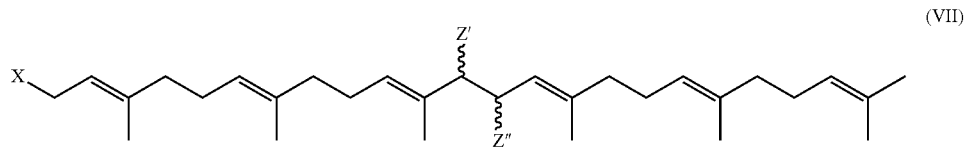

wherein
X represents halogen,
one of Z' and Z" is H and the other is a phenylsulfonyl —SO$_2$Ph group,
is obtained in the process comprising the steps of:
(i) alkylating the two triprenyl units of formulae (III) and (IV)

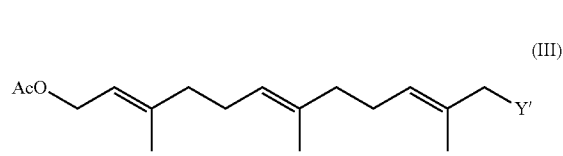

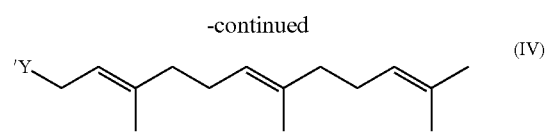

wherein:
if one of the Y' and Y" represents the phenylsulfonyl —SO$_2$Ph group, then the other Y' Y" represents the halogen atom,
in the presence of a strong base, to yield the compound of formula (V)

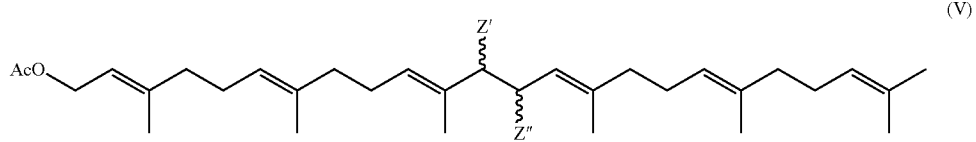

wherein one of Z' and Z" represents H and the other represents the phenylsulfonyl —SO$_2$Ph group,
(ii) removing acetyl and, optionally, phenylsulfonyl groups from the compound of formula (V), to yield the hexaprenol derivative of formula (VI)

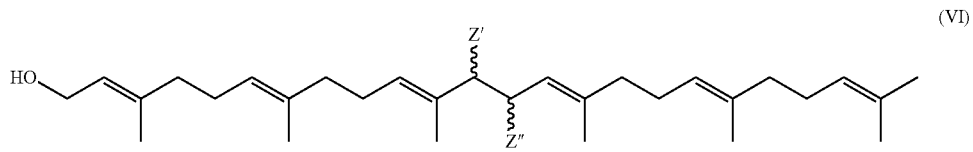

wherein one of Z' and Z" represents H and the other represents the phenylsulfonyl —SO$_2$Ph group,
(iii) reacting the compound of formula (VI) with a halogenating agent, to yield the phenylosulfonyl-hexaprenyl halide of formula (VII)

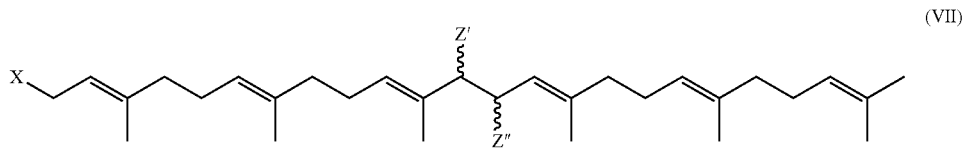

X represents halogen atom, and
Z' and Z" have the meaning defined above for the formula (VI).

7. The process according to claim 1, wherein the alkylating agent is the phenylsulfonyl hexaprenyl halide of the formula (VII)

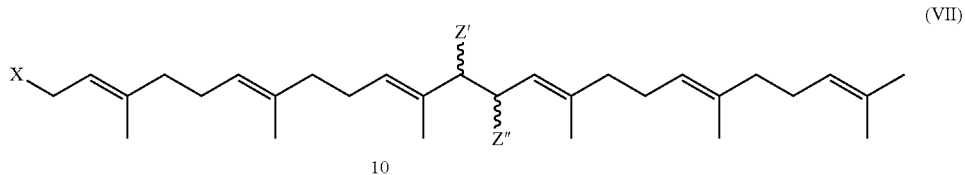

(VII)

wherein
X represents bromine atom,
one of Z' and Z" represents H, and the other of Z' and Z" is the phenylsulfonyl —SO$_2$Ph group.

8. A process for the preparation of MK-7 type of vitamin K$_2$, represented by the formula (I)

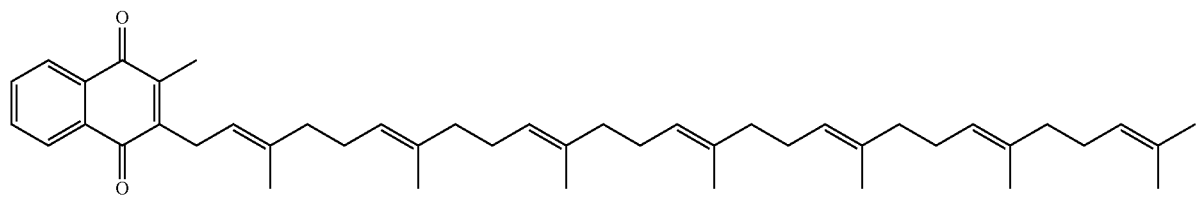

(I)

consisting of the steps of:
(a') alkylating the two triprenvl units of formulae (III) and (IV)

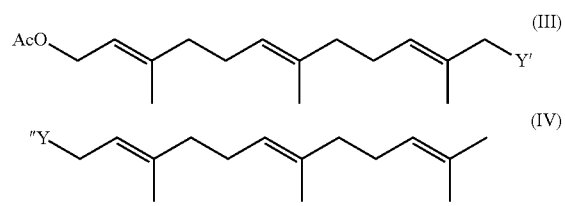

(III)

(IV)

wherein:
if one of the Y' and Y" represents the phenylsulfonyl —SO$_2$Ph group, then the other Y' Y" represents the halogen atom,
in the presence of strong base, to yield the compound of formula (V)

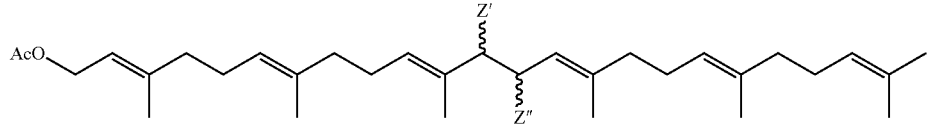

(V)

wherein one of Z' and Z" represents H and the other represents the phenylsulfonyl SO$_2$Ph group,
(b') removing the acetyl and, optionally, phenylsulfonyl groups from the compound of formula (V), to yield the hexaprenol derivative of formula (VI)

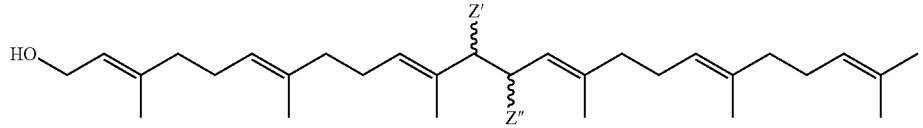

(VI)

wherein each of Z' and Z" represents H, or one of Z' and Z" represents H and the other represents the phenylsulfonyl —SO$_2$Ph group, (c') optionally, removing the phenylsulfonyl group Z' or Z", to yield the hexaprenol derivative of formula (VI)

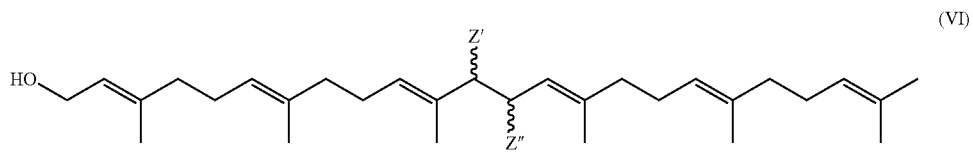

(VI)

wherein
X represents halogen atom, and
Z' and Z" both represent H,
(d') reacting the compound of formula (VI) with a halogenating reagent, to yield the phenylosulfonyl hexaprenyl halide of formula (VII)

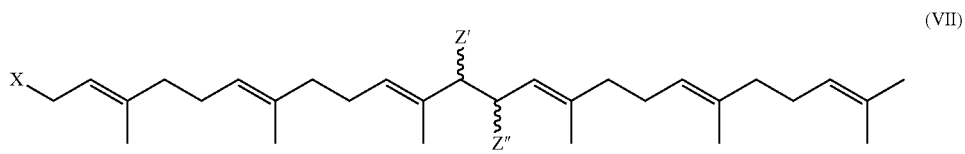

(VII)

wherein
X represents halogen atom, and
Z' and Z" have the meaning defined above for the formula (VI),
(e') reacting an a-sulfonyl carbanion generated in situ from the phenylsulfone of monoprenylmenadiol derivative of formula (II)

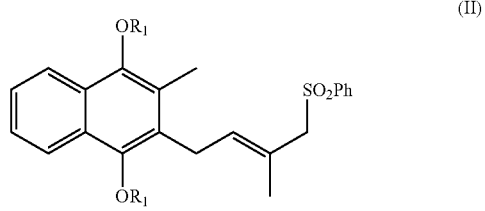

(II)

wherein R$_1$ represents C$_2$-alkyl, and wherein said phenylsulfone of monoprenylmenadiol derivative of formula (II) is in a crystalline form;
with the hexaprenyl halide of formula (VII)

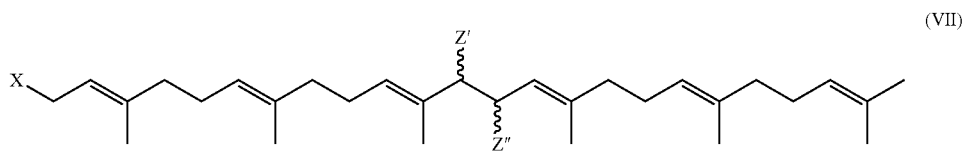

(VII)

wherein
X represents halogen,
one of Z' and Z" is H and the other is phenylsulfonyl —SO₂Ph group, as an alkylating agent;
to yield the phenylsulfonyl derivative of menadiol of the formula (VIII)

(h') optionally, purifying the crude menadione derivative of formula (I) to yield pure MK-7.

9. The process according to claim 8, wherein the acetyl groups are removed by means of hydrolysis under the basic conditions.

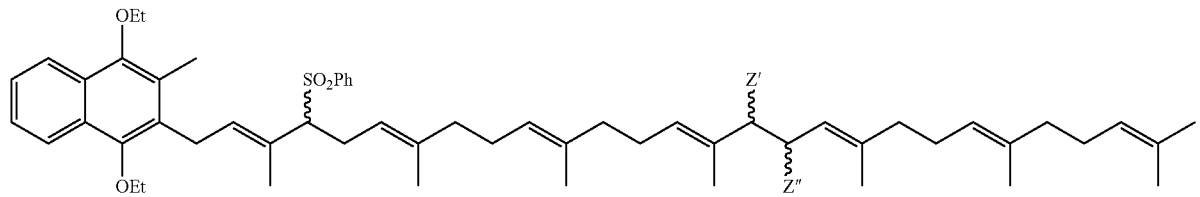

(VIII)

wherein R₁, Z' and Z" have the meaning defined above for the formula (VI), (f) removing the phenylsulfonyl groups by the reductive elimination, to yield the menadiol derivative of formula (IX), 10. The process according to claim 8 wherein the steps of: (a') alkylating the triprenyl units, and (b') removing the acetyl and phenylsulfonyl groups, are carried out in a "one pot" process, without isolating the intermediates out of the reaction mixture.

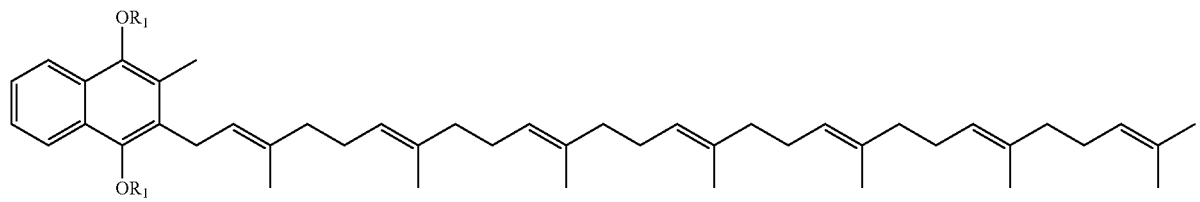

(IX)

(g') subjecting the menadiol derivative of formula (IX) to an oxidative deetherification, to yield the crude menadione derivative of formula (I)

11. The process according to claim 8, wherein the phenylsulfonyl groups are removed in the reaction of the reductive elimination by means of an alkali metal borohy-

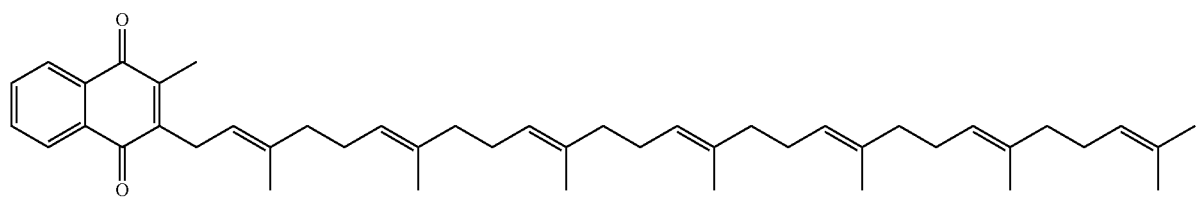

(I)

dride in the presence of an alkali metal(II) dihalides complexes with bidentate ligands of phenylphosphine type of the general formula [M{Ph$_2$P(CH$_2$)$_n$PPh$_2$X$_2$}], wherein n=2-5, X=Cl or Br, and M=Co, Ni or Pd, as catalysts.

12. The process according to claim 11, wherein the said phenylsulfonyl groups are removed by means of lithium triethylborohydride in the presence of Pd(dppe)Cl$_2$ complex,

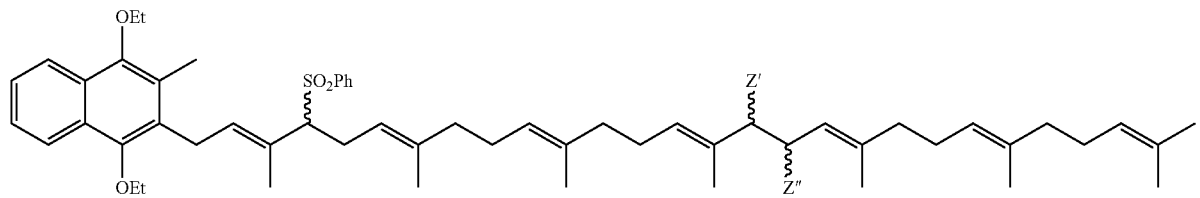

(VIII)

wherein dppe represents 1,2-bis(diphenylphosphine)ethane, or Pd(dppp)Cl$_2$, wherein dppp represents 1,3-bis(diphenylphosphine)propane.

13. The process according to claim 8, wherein the oxidative Deetherification is accomplished with the use of cerium ammonium nitrate.

14. A compound 1, 4-diethoxy-2-methyl naphthalene

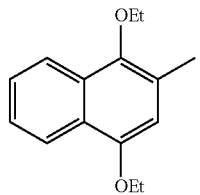 [SMILES: CCOc1cc(C)c(OCC)c2ccccc12]

in a crystalline form showing characteristic peaks in X-ray powder diffraction (XRPD) pattern recorded with CuKα, λ=1.54056 Å of relative intensities I/I$_0$>20% at the following reflection angles 2 ⊖: 9.86 and 19.76 ±0.2°.

15. A compound 1,4-diethoxy-2-methyl-3-[(2E)-3-methyl-4-(phenylsulfonyl)-2-buten-1-yl]naphthalene

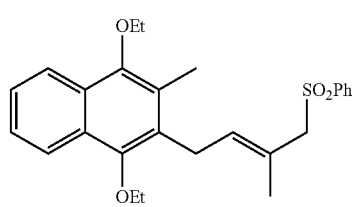

(II)

in a crystalline form showing characteristic peaks in an X-ray powder diffraction (XRPD) pattern recorded with CuKα, λ=1.54056 Å wave length, represented by the relative intensities of diffraction lines I/I$_0$>20% at the following reflection angles 2 ⊖:10.29, 12.69, 17.57, 19.62, 20.61, 21.05, 21.73, 23.25, 24.38i 25.52 ±0.2°.

16. Intermediate compounds of the general formula (VIII)

wherein
Z' and Z" both represent H, or one of Z' and Z" is H and the other is the phenylsulfonyl —SO$_2$Ph group.

17. The process according to claim 1, wherein X is bromine.

18. The process according to claim 2, wherein the alkali metal hexamethyldisilazyde is sodium hexamethyldisilazyde and/or the polar aprotic solvent is tetrahydrofuran, dimethylformamide, hexamethylophosphoramide or a mixture thereof.

19. The process according to claim 6, wherein X is bromine.

20. The process according to claim 8, wherein X is bromine.

21. The compound according to claim 16, wherein Z' is SO$_2$Ph and Z" is H.

22. The process according to claim 1, wherein said phenylsulfone of monoprenylmenadiol derivative of formula (II) is purified by crystallization in ethanol.

23. The process according to claim 1, wherein the phenylsulfone of monoprenylmenadiol derivative of formula (II) is purified by crystallization prior to the reaction in step (a).

24. The process according to claim 8, wherein the phenylsulfone of monoprenylmenadiol derivative of formula (II) is purified by crystallization prior to the reaction in step (e').

* * * * *